United States Patent
Neal et al.

(10) Patent No.: US 11,730,359 B2
(45) Date of Patent: Aug. 22, 2023

(54) OPTICAL IMAGING AND MEASUREMENT SYSTEMS AND METHODS FOR CATARACT SURGERY AND TREATMENT PLANNING

(71) Applicant: AMO Development, LLC, Irvine, CA (US)

(72) Inventors: Daniel Neal, Tijeras, NM (US); Thomas D. Raymond, Edgewood, NM (US); Richard J. Copland, Albuquerque, NM (US); Wei Xiong, Albuquerque, NM (US); Paul D. Pulaski, Albuquerque, NM (US); Stephen Farrer, Albuquerque, NM (US); Carmen Canovas Vidal, Groningen (NL); Daniel Hamrick, Cedar Crest, NM (US)

(73) Assignee: AMO Development, LLC, Irvine, CA (US)

( * ) Notice: Subject to any disclaimer, the term of this patent is extended or adjusted under 35 U.S.C. 154(b) by 499 days.

(21) Appl. No.: 16/714,652

(22) Filed: Dec. 13, 2019

(65) Prior Publication Data
US 2020/0113433 A1    Apr. 16, 2020

Related U.S. Application Data

(62) Division of application No. 14/969,264, filed on Dec. 15, 2015, now Pat. No. 10,506,923.
(Continued)

(51) Int. Cl.
*A61B 3/10*    (2006.01)
*A61F 9/008*    (2006.01)
(Continued)

(52) U.S. Cl.
CPC ............ *A61B 3/102* (2013.01); *A61B 3/0025* (2013.01); *A61B 3/0091* (2013.01);
(Continued)

(58) Field of Classification Search
CPC ..... A61B 3/102; A61B 3/0025; A61B 3/0091; A61B 3/1005; A61B 3/1015; A61B 3/107;
(Continued)

(56) References Cited

U.S. PATENT DOCUMENTS 5,777,719 A    7/1998    Williams et al.
6,550,917 B1    4/2003    Neal et al.
(Continued)

FOREIGN PATENT DOCUMENTS

EP    2232198 B1    6/2015
WO    0158339 A2    8/2001
(Continued)

OTHER PUBLICATIONS

Canovas C., et al., "Customized Eye Models for Determining Optimized Intraocular Lenses Power," Biomedical Optics Express, Jun. 1, 2011, vol. 2 (6), pp. 1649-1662.
(Continued)

*Primary Examiner* — Stephone B Allen
*Assistant Examiner* — Rahman Abdur
(74) *Attorney, Agent, or Firm* — Johnson & Johnson Surgical Vision, Inc.

(57) ABSTRACT

An optical measurement system and apparatus for carrying out cataract diagnostics in an eye of a patient includes a Corneal Topography Subsystem, a wavefront aberrometer subsystem, and an eye structure imaging subsystem, wherein the subsystems have a shared optical axis, and each subsystem is operatively coupled to the others via a controller. The eye structure imaging subsystem is preferably a fourierdo-
(Continued)

main optical coherence tomographer, and more preferably, a swept source OCT.

9 Claims, 17 Drawing Sheets

Related U.S. Application Data

(60) Provisional application No. 62/197,539, filed on Jul. 27, 2015.

(51) Int. Cl.

| | |
|---|---|
| *A61B 3/00* | (2006.01) |
| *A61B 3/107* | (2006.01) |
| *A61B 3/11* | (2006.01) |
| *A61B 3/117* | (2006.01) |
| *A61B 3/12* | (2006.01) |
| *A61B 3/18* | (2006.01) |
| *G02B 5/30* | (2006.01) |
| *G02B 27/28* | (2006.01) |

(52) U.S. Cl.
CPC ............ *A61B 3/1005* (2013.01); *A61B 3/107* (2013.01); *A61B 3/1015* (2013.01); *A61B 3/112* (2013.01); *A61B 3/117* (2013.01); *A61B 3/1173* (2013.01); *A61B 3/1225* (2013.01); *A61B 3/18* (2013.01); *A61F 9/008* (2013.01); *G02B 5/3083* (2013.01); *G02B 27/286* (2013.01); *A61F 2009/0087* (2013.01); *A61F 2009/00887* (2013.01)

(58) Field of Classification Search
CPC ....... A61B 3/112; A61B 3/117; A61B 3/1173; A61B 3/1225; A61F 9/008; A61F 2009/0087; A61F 2009/00887; A61F 9/00812; G02B 5/3083; G02B 27/286
USPC .......................................................... 351/205
See application file for complete search history.

(56) References Cited

U.S. PATENT DOCUMENTS

| | | |
|---|---|---|
| 6,908,196 B2 | 6/2005 | Herekar et al. |
| 7,455,407 B2 | 11/2008 | Neal et al. |
| 7,553,022 B2 | 6/2009 | Neal et al. |
| 7,980,699 B2 | 7/2011 | Neal et al. |
| 7,988,292 B2 | 8/2011 | Neal et al. |
| 8,126,246 B2 | 2/2012 | Farrer et al. |
| 8,260,024 B2 | 9/2012 | Farrer et al. |
| 8,430,508 B2 | 4/2013 | Weeber |
| 8,444,267 B2 | 5/2013 | Weeber et al. |
| 8,480,228 B2 | 7/2013 | Weeber |
| 8,623,081 B2 | 1/2014 | Canovas et al. |
| 8,696,119 B2 | 4/2014 | Van et al. |
| 8,696,120 B2 | 4/2014 | Van et al. |
| 8,746,882 B2 | 6/2014 | Canovas et al. |
| 2003/0214628 A1 | 11/2003 | Patel |
| 2009/0161090 A1* | 6/2009 | Campbell ............... G01B 11/25 351/212 |
| 2011/0102802 A1 | 5/2011 | Izatt et al. |
| 2011/0118609 A1 | 5/2011 | Goldshleger et al. |
| 2011/0299034 A1 | 12/2011 | Walsh et al. |
| 2012/0044454 A1* | 2/2012 | Canovas Vidal .... A61B 3/0025 703/2 |
| 2012/0172854 A1 | 7/2012 | Raymond et al. |
| 2013/0201445 A1* | 8/2013 | Das ....................... A61F 2/1654 351/159.73 |
| 2013/0226294 A1 | 8/2013 | Van et al. |
| 2013/0282116 A1 | 10/2013 | Van et al. |
| 2013/0335701 A1 | 12/2013 | Canovas et al. |
| 2014/0253877 A1 | 9/2014 | Li et al. |
| 2014/0347629 A1 | 11/2014 | Donitzky et al. |
| 2015/0131053 A1 | 5/2015 | Copland et al. |
| 2015/0172854 A1 | 6/2015 | Stogaitis et al. |

FOREIGN PATENT DOCUMENTS

| | | |
|---|---|---|
| WO | 2008112292 A1 | 9/2008 |
| WO | 2013028992 A1 | 2/2013 |
| WO | 2014172621 A2 | 10/2014 |

OTHER PUBLICATIONS

Kob S., et al., "Simultaneous Measurement of Tear Film Dynamics Using Wave front Sensor and Optical Coherence Tomography," Investigative Ophthalmology & Visual Science, Jul. 2010, vol. 51 (7), pp. 3441-3448.

Kottig F., et al., "An Advanced Algorithm for Dispersion Encoded Full Range Frequency Domain Optical Coherence Tomography," Optics Express, 2012, vol. 20 (22), pp. 24925-24948.

Liu H., et al., "Measurement of the Time Course of Optical Quality and Visual Deterioration during Tear Break-Up," Investigative Ophthalmology & Visual Science, Jun. 2010, vol. 51 (6), pp. 3318-3326.

Mejia-Barbosa Y., et al., "Object Surface For Applying A Modified Hartmann Test To Measure Corneal Topography," Applied Optics, Nov. 1, 2001, vol. 40 (31), pp. 5778-5786.

Wojtkowski M., et al., "Full Range Complex Spectral Optical Coherence Tomography Technique in Eye Imaging," Optics Letters, 2002, vol. 27 (16), pp. 1415-1417.

* cited by examiner

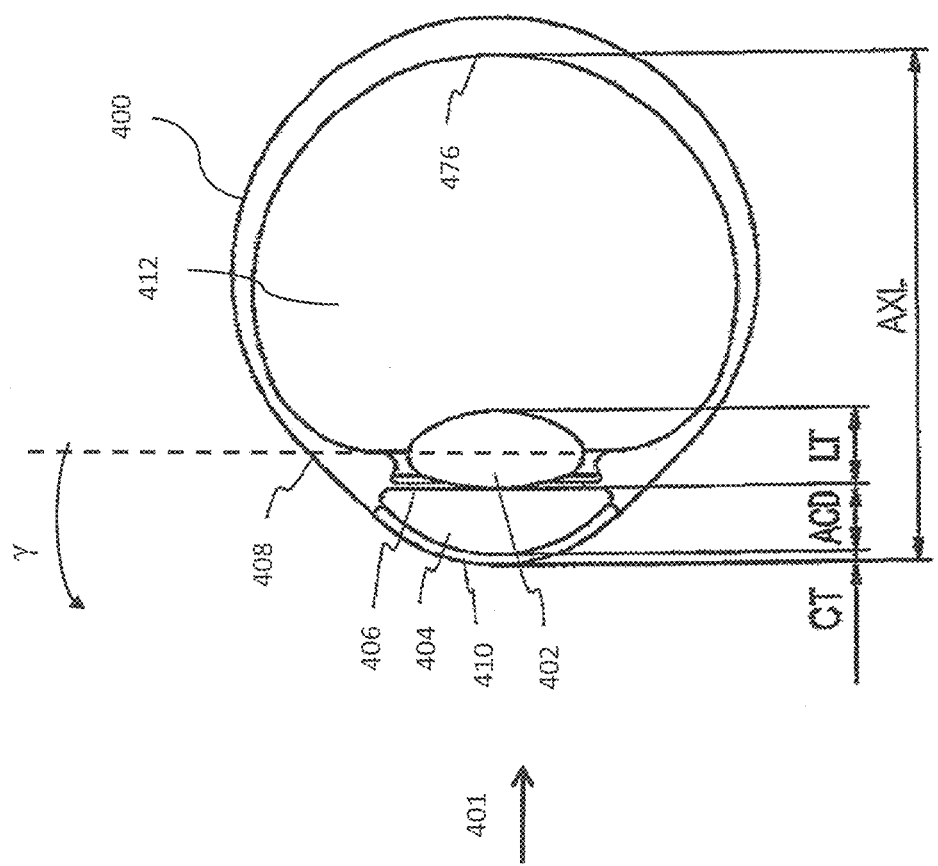

OPTICAL IMAGING AND MEASUREMENT SYSTEMS AND METHODS FOR CATARACT SURGERY AND TREATMENT PLANNING

RELATED APPLICATIONS

This application is a divisional of and claims priority to U.S. patent application Ser. No. 14/969,264, filed Dec. 15, 2015, which is a non-provisional application and claims the benefit under 35 U.S.C. § 119(e) of U.S. Provisional Application Ser. No. 62/197,539, filed Jul. 27, 2015, which is incorporated herein in its entirety by reference.

BACKGROUND

Cataract extraction is a frequently performed surgical procedure. A cataract forms through opacification of the eye's crystalline lens. The cataract scatters light passing through the lens, and may perceptibly degrade vision. Generally, a cataract can vary in degree from slight to complete opacity. Early in the development of an age-related cataract, the power of the lens may increase, causing near-sightedness (myopia). Over time, the gradual yellowing and opacification of the lens may reduce the perception of blue colors as shorter wavelengths are more strongly absorbed and scattered within the cataractous crystalline lens. As the cataract formation gradually progresses, the patient may experience progressive vision loss.

Cataract treatment may involve surgically removing the opaque crystalline lens, and replacing it with an artificial intraocular lens (IOL). Each year, an estimated 15 million cataract surgeries are performed worldwide. Cataract surgery can be performed using a technique called phacoemulsification in which an ultrasonic tip with associated irrigation and aspiration ports is used to sculpt the relatively hard nucleus of the lens to facilitate removal through an opening made in the anterior lens capsule. The nucleus of the crystalline lens is contained within an outer membrane of the lens referred to as the lens capsule. To access the lens nucleus, surgeons first perform a manual continuous curvilinear capsulohexis (CCC) procedure to form a circular hole in the anterior side of the lens capsule. Alternatively, surgeons may use a laser surgical system to perform the anterior capsulotomy to gain access to the lens nucleus. The surgical laser beam may also be used to fragment the cataractous crystalline lens before it is aspirated out of the eye. After the cataractous lens is removed, a synthetic foldable intraocular lens (IOL) can be inserted into the remaining lens capsule of the eye.

Planning a cataract treatment can be challenging. There is significant variation between patients in many important eye biometric parameters, each of which may affect surgical planning, treatment, and outcome. Moreover, many patients may have biometric configurations, including for example, corneal lower order and higher order aberrations, extreme axial lengths, and/or previous corneal refractive treatments such as LASIK, which may also affect surgical planning, treatment, and outcome. For example, with respect to eye aberrations, some patients have near-sightedness (myopia), far-sightedness (hyperopia), or astigmatism. Near-sightedness occurs when light focuses in front of the retina, while far-sightedness occurs when light refracts to a focus behind the retina. Astigmatism occurs when the corneal curvature is unequal in two or more directions. Various surgical methods have been developed and used to treat these types of aberrations. Ideally, for best results and outcome, a cataract surgeon would have access to not only ocular biometry information, but also to information on the eye's anterior corneal surface, posterior corneal surface, anterior lens surface, posterior lens surface, lens tilt, lens thickness, and lens position in order to plan cataract treatment pre-operatively, and/or to assess the post-operative refractive state of a patient's eye with the implanted IOL.

A variety of optical diagnostic systems have been developed, each of which provides a limited subset of the desired measurements. Thus, currently most patients have various measurements performed on different devices if the measurements are taken at all. There is a significant disadvantage, however, to using multiple measurement devices in cataract planning because the patient's eye may be in different positions during each of the measurements, and/or it may have changed between the different measurements, or the measurement may have been made under different conditions. Further, there may be no way to combine or fuse the data sets from different devices to obtain a single, three-dimensional model of the patient's eye. Hence, it can be often difficult to apply advanced vision modeling techniques, such as ray tracing, because the current diagnostic environment is often inadequate to reliably produce the three-dimensional models necessary for accurate vision modeling.

As a result, there is an ongoing need for an improved optical imaging, measurement, and diagnostic system that can obtain most, if not all, of the necessary biometric and structural features of a patient's eye with the patient's eye in a single orientation within a brief period of time, that can fuse the data obtained from various optical techniques to achieve an accurate three-dimensional model of a patient's eye, and that can utilize advanced vision modeling techniques, such as ray tracing or other power calculation techniques, to improve cataract planning and outcome evaluation.

SUMMARY OF THE INVENTION

This disclosure provides embodiments for improved optical measurement systems and methods for carrying out imaging and measurements used for diagnostics, treatment planning, and IOL placement for cataract treatment and surgery.

An eye imaging and measurement system for planning a cataract treatment in a patient's eye according to one embodiment comprises: a Corneal Topography Subsystem, a wavefront aberrometer subsystem, and an eye structure imaging subsystem, wherein the subsystems have a shared optical axis, and each subsystem is operatively coupled to the others via a controller. The eye structure imaging subsystem is selected from the group consisting of an optical coherence tomographer (OCT), a Scheimpflug imager, a fluorescence imager, a structured lighting imager, a wavefront tomographer, and an ultrasound imager. The eye structure imaging subsystem is an optical coherence tomographer, including for instance, a Fourier domain optical coherence tomographer, a spectral domain optical coherence tomographer, or a swept source optical coherence tomographer.

In many embodiments, the eye imaging and measurement system comprises an iris imaging subsystem operatively coupled to the controller.

In many embodiments, the eye imaging and measurement system comprises a posterior corneal astigmatism imaging and measurement subsystem operatively coupled to the controller.

In many embodiments, the eye imaging and measurement device comprises a fixation target subsystem operatively coupled to the controller. This target allows for fixating the eye during on axis measurements. In other embodiments, this target can be used to perform off-axis measurements at different eccentricities.

In many embodiments, the controller is coupled to an Optical Coherence Tomography (OCT) subsystem configured to sequentially scan the eye in a plurality of OCT scan patterns, each scan pattern being at a different axial depth of a patient's eye. The plurality of scan patterns comprise an anterior segment OCT scan pattern at or near a location of a cornea, a lenticular OCT scan pattern at or near a location of a lens, and a retinal OCT scan patter at or near a location of a retina. The plurality of imaging scan patterns preferably comprises an anterior segment OCT scan pattern suitable to measure a plurality of an anterior corneal surface, a corneal pachymetry, a central corneal thickness, and an anterior chamber depth of a patient's eye. The plurality of imaging scan patterns preferably also comprises a lenticular OCT scan segment scan pattern suitable to measure a plurality of a lens thickness, an anterior lens surface, a posterior lens surface, and a lens surface tilt and decentration. The plurality of imaging scan patterns comprises a retinal OCT segment scan pattern suitable to measure at least one of an axial length and a retinal layer thickness information. These measurements may also be done post-operatively, allowing the measurement of IOL axial position, tilt, and decentration, so that the instrument allows for evaluation of postoperative outcomes and secondary treatment planning, if needed.

In many embodiments, the eye imaging and measurement system comprises a memory operable to store data acquired from each of the Corneal Topography Subsystem, the wavefront sensor subsystem, and the Optical Coherence Tomography subsystem, wherein the stored data includes a plurality of ocular biometry information, anterior corneal surface information, posterior corneal surface information, anterior lens surface information, and posterior lens surface information, lens tilt information, and lens position information. The ocular biometry information preferably comprises a plurality of a central corneal thickness (CCT), an anterior chamber depth (ACD), a pupil diameter (PD), a white to white distance (WTW), a lens thickness (LT), an axial length (AXL), and retinal layer thickness.

In many embodiments, the eye imaging and measurement system further comprises a memory operable to store Intraocular Lens ("IOL") Data, the IOL data including a plurality of dioptic power, anterior and posterior radius, IOL thickness, refractive index and dispersion, asphericity, toricity, echelette features, haptic angulation, and lens filter.

In many embodiments, the eye imaging and measurement system further comprises a memory operable to store intraocular lens ("IOL") model data for a plurality of IOL models, IOL model having associated with a plurality of predetermined parameters selected from the group consisting of dioptic power, anterior and posterior radius, IOL thickness, refractive index, asphericity, toricity, echelette features, haptic angulation, and lens filter.

An improved system for selecting an intraocular lens (IOL) for implantation, comprises: a memory operable to store data acquired from each of the Corneal Topography Subsystem, the wavefront sensor subsystem, and the Optical Coherence Tomography subsystem, wherein the stored data includes a plurality of ocular biometry information, anterior corneal surface information, posterior corneal surface information, anterior lens surface information, posterior lens surface information, lens tilt information, and lens position information; the memory further operable to store intraocular lens ("IOL") model data for a plurality of IOL models, the IOL model having associated with it a plurality of predetermined parameters selected from the group consisting of dioptic power, anterior and posterior radius, IOL thickness, refractive index, asphericity, toricity, echelette features, haptic angulation, and lens filter; and a processor coupled to the memory, the processor deriving the treatment of the eye of the patient applying, for each of the plurality of identified IOL models, to: (1) predict a position of one of the identified IOL models when implanted in the subject eye, based on the plurality of characteristics; (2) simulate the subject eye by means of ray tracing for a plurality of IOL predetermined parameters and the predicted IOL position; (3) based on that, select an IOL spherical equivalent (SE) and cylinder (C) power, as well as determine the optimum IOL orientation based on said eye model; (4) propose the selected IOL power for one or more IOL models from the plurality of IOLs corresponding to the optimized IOL(s) based on predetermined criteria; and (5) show the simulated optical quality and/or visual performance provided by each of the proposed IOL models for distance and/or for any other vergence or field angle.

An improved method for selecting an intraocular lens may include the calculation of the posterior corneal astigmatism and total corneal power of the eye. An accurate method to calculate these two quantities may be comprised of a first step of measuring the anterior corneal shape with a topographer, a second step of measuring a corneal thickness map with a scanning optical coherence tomographer, and a third step of adding the thickness map to the anterior surface shape to obtain the shape of the posterior surface. For highest accuracy, the bending of the optical coherence beam on the anterior corneal surface may be calculated using Snell's law at each location across the cornea prior to the step of adding the thickness map to the anterior cornea shape. After the determination of posterior corneal shape, the posterior corneal astigmatism and total corneal power may be calculated using standard optical ray tracing techniques.

A method of selecting an intraocular lens (IOL) to be implanted in a subject eye, or alternatively, a tangible computer-readable storage device storing computer instructions which, when read by a computer, cause the computer to perform the method, comprises: measuring a plurality of eye characteristics comprising ocular biometry information, anterior corneal surface information, posterior corneal surface information, anterior lens surface information, posterior lens surface information, lens tilt information, and lens position information; and for each of Intraocular Lens ("IOL") model having associated with it a plurality of predetermined parameters selected from the group consisting of dioptic power, refractive index, anterior and posterior radius, IOL thickness, asphericity, toricity, echelette design, haptic angulation, and lens filter: (1) modeling the subject eye with the intraocular lens; (2) simulating the subject eye based on the plurality of IOL predetermined parameters and the predicted IOL position; (3) performing a ray tracing and an IOL spherical equivalent (SE) and cylinder (C) power calculation, as well as determine the optimum IOL orientation based on said eye model; and (4) proposing one IOL power for one or more IOL models from the plurality of IOLs corresponding to the optimized IOL(s) based on predetermined criteria; and optionally, (5) show the simulated optical quality and/or visual performance provided by each of the proposed IOL models for distance and/or for any other vergence.

A method, or alternatively, a tangible computer-readable storage device storing computer instructions which, when read by a computer, cause the computer to perform the method, comprising: (1) receiving a plurality of eye characteristics comprising ocular biometry information, anterior corneal surface information, posterior corneal surface information, anterior lens surface information, and posterior lens surface information, lens tilt information and lens position information; (2) for each of Intraocular Lens ("IOL") model having associated with it a plurality of predetermined parameters selected from the group consisting of dioptic power, refractive index, anterior and posterior radius, IOL thickness, asphericity, toricity, echelette design, haptic angulation, and lens filter: simulating a geometry of the subject eye with each of the plurality of intraocular lenses (IOL) implanted, in accordance with the plurality of eye characteristics; (3) performing a ray tracing and an IOL spherical equivalent (SE) and cylinder (C) power calculation, as well as determine the optimum IOL orientation based on said eye model; (4) proposing one IOL power for one or more IOL models from the plurality of IOLs corresponding to the optimized IOL(s) based on predetermined criteria; and, optionally (5) showing the simulated optical quality and/or visual performance provided by each of the proposed IOL models for distance and/or for any other vergence.

A method of predicting the intraocular lens position comprising: determining a plurality of eye characteristics before cataract surgery, comprising ocular biometry information, anterior corneal surface information, posterior corneal surface information, anterior lens surface information, posterior lens surface information, lens tilt information, and lens position information; determining a plurality of eye characteristics after cataract surgery, comprising ocular biometry information, anterior corneal surface information, posterior corneal surface information, anterior lens surface information, and posterior lens surface information, IOL tilt information and IOL position information; calculating or measuring, based on a mathematical relationship, a distance from the apex or from the retina to a plane of the intraocular lens after an ocular surgical procedure; calculating an optical power of the intraocular lens suitable for providing a predetermined refractive outcome; wherein a mathematical relationship is found between the preoperative and postoperative eye characteristics that accurately predicts the measured distance from the apex or from the retina to the plane where the intraocular lens is.

An improved system for planning a treatment of an eye of a patient, the system comprising: a memory operable to store eye measurement data comprising ocular biometry information, anterior corneal surface information, posterior corneal surface information, anterior lens surface information, posterior lens surface information, lens tilt information, and lens position information; a processor coupled to the memory, the processor deriving the treatment of the eye of the patient applying an effective treatment transfer function, wherein the effective treatment transfer function is derived from, for each of a plurality of prior eye treatments, a correlation between a pre-treatment vector characterizing the eye measurement data before treatment, and a post-treatment vector characterizing post-treatment eye measurement data of the associated eye; an output coupled to the processor so as to transmit the treatment to facilitate improving refraction and/or higher order aberration and/or optical quality of the eye of the patient for one or multiple vergences and/or field angles. The processor preferably comprises tangible media embodying machine readable instructions for implementing the derivation of the treatment.

An improved method for planning a refractive treatment of an eye of a patient, the method comprising: measuring a plurality of ocular biometry information, anterior corneal surface information, posterior corneal surface information, anterior lens surface information, and posterior lens surface information, lens tilt information, and lens position information.

A method of customizing at least one parameter of an intraocular lens, comprising: measuring a plurality of eye characteristics comprising ocular biometry information, anterior corneal surface information, posterior corneal surface information, anterior lens surface information, posterior lens surface information, lens tilt information, and lens position information; determining a desired postoperative condition of the eye; empirically calculating a post-operative condition of the eye based at least partially on the measured eye characteristics; and predictively estimating, in accordance with an output of said empirically calculating the post-operative condition and the eye characteristics, the at least one parameter of the intraocular lens to obtain the desired postoperative condition.

A method of adjusting the refraction in an eye of a patient who has undergone cataract surgery comprising: measuring a plurality of post-operative eye characteristics in an eye of a patient who has previously undergone cataract surgery, the eye characteristics comprising ocular biometry information, anterior corneal surface information, posterior corneal surface information, anterior lens surface information, and posterior lens surface information, lens tilt information and lens position information; identifying a plurality of corrective procedure based at least partially on one of (1) a comparison of at least one measured pre-operative eye characteristic and the corresponding measured post-operative eye characteristic; and (2) a comparison of at least one predicted post-operative eye characteristic and the corresponding measured post-operative eye characteristic; for each of a plurality of corrective procedures: modeling the subject eye with the corrective procedure; modeling the subject eye based on the corrective procedure; performing one of a ray tracing and a power calculation based on said eye model; and selecting a corrective procedure from the plurality of IOL models corresponding to the optimized IOL based on a predetermined criteria.

In some embodiments, the system further comprises a processor configured to execute an algorithm. The algorithm comprises, for each of the IOL models: (1) modeling the subject's eye with an intraocular lens corresponding to the IOL model and the measured characteristics of the subject's eye; (2) simulating the subject's eye based on the plurality of IOL predetermined parameters and the predicted IOL position; (3) performing one of a ray tracing and a power calculation based on said model of the subject's eye; and (4) selecting an IOL from the plurality of IOL models corresponding to the optimized IOL based on a predetermined criteria.

In some embodiments, the system further comprises a processor configured to execute an algorithm. The algorithm comprises: determining a desired postoperative condition of the subject's eye; empirically calculating a post-operative condition of the subject's eye based at least partially on the one or more measured characteristics of the subject's eye; and predictively estimating, in accordance with an output of said empirically calculating and the eye characteristics, at least one parameter of an intraocular lens for implantation into the subject's eye to obtain the desired postoperative condition.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by the structure particularly pointed out in the written description, claims and the appended drawings.

BRIEF DESCRIPTION OF THE DRAWINGS

The novel features of the invention are set forth with particularity in the appended claims. A better understanding of the features and advantages will be facilitated by referring to the following detailed description that sets forth illustrative embodiments using principles of the invention, as well as to the accompanying drawings, in which like numerals refer to like parts throughout the different views. Like parts, however, do not always have like reference numerals. Further, the drawings are not drawn to scale, and emphasis has instead been placed on illustrating the principles of the invention. All illustrations are intended to convey concepts, where relative sizes, shapes, and other detailed attributes may be illustrated schematically rather than depicted literally or precisely.

FIG. 5 is a schematic drawing of a human eye.

DETAILED DESCRIPTION

Exemplary embodiments of optical measurement systems and methods for cataract diagnostics to illustrate various aspects and advantages of these devices and methods are described below. It should be understood, however, that these devices and methods involve principles that can be employed in a variety of other contexts, and therefore, the novel devices and method disclosed and claimed here should not be construed as being limited to the examplary embodiments described below.

Figure 1C:
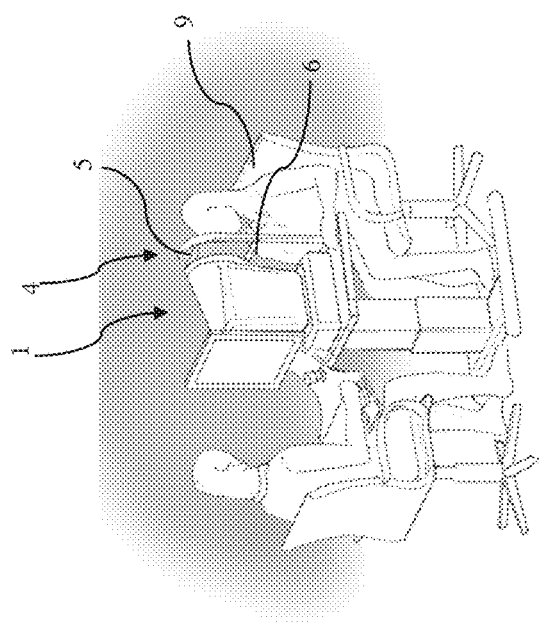
FIG. 1C illustrates a side perspective view showing an optical measurement system according to many embodiments.
Figure 1A:
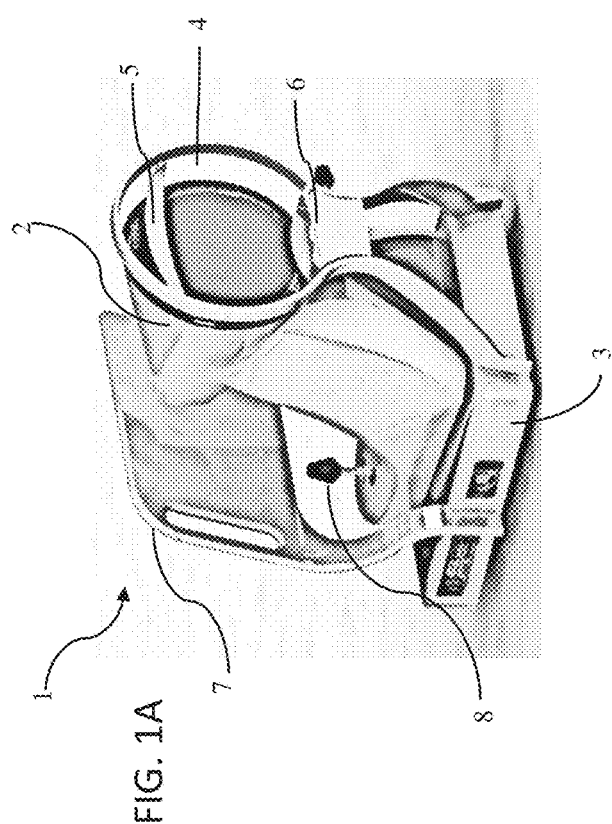
FIG. 1A illustrates a front perspective view showing an optical measurement system according to many embodiments.
Figure 1B:
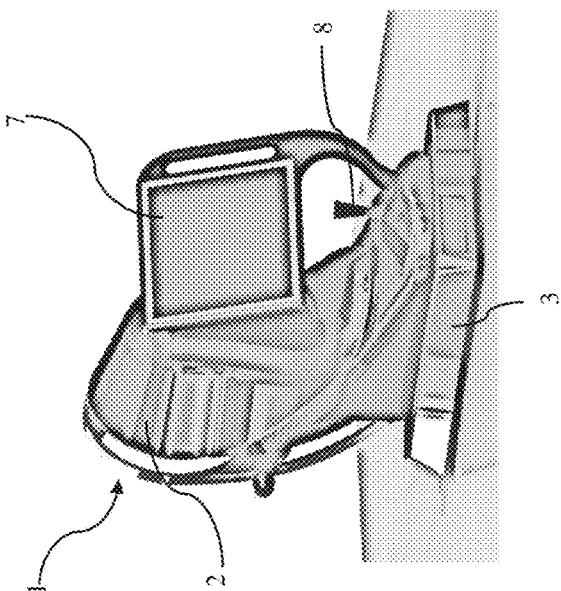
FIG. 1B illustrates a rear perspective view showing an optical measurement system according to many embodiments.

As shown in FIGS. 1A-1C, an optical measurement system 1, according to many embodiments, is operable to provide for a plurality of measurements of the human eye, including measurements of the cornea, the lens capsule, the lens and the retina. The main unit 2 comprises a base 3 and includes many primary subsystems of many embodiments of the system 1. For example, externally visible subsystems include a touch-screen display control panel 7, a patient interface assembly 4 and a joystick 8.

The patient interface 4 preferably includes one or more structures configured to hold a patient's head in a stable, immobile and preferably comfortable position during the diagnostic measurements while also maintaining the eye of the patient in a suitable alignment with the diagnostic system. In a particularly preferred embodiment, the eye of the patient remains in substantially the same position relative to the diagnostic system for all diagnostic and imaging measurements performed by the system 1.

In one embodiment, the patient interface includes a chin support 6 and/or a forehead rest 5 configured to hold the head of the patient in a single, uniform position suitably aligned with respect to the system 1 throughout the diagnostic measurement. As shown in FIG. 1C, the optical measurement system 1 is preferably disposed so that the patient may be seated in a patient chair 9. The patient chair 9 can be configured to be adjusted and oriented in three axes (x, y, and z) so that the patent's head can be at a suitable height and lateral position for placement on the patient interface.

In many embodiments, the system 1 may include external communication connections. For example, the system 1 can include a network connection (e.g., an RJ45 network connection) for connecting the system 1 to a network. The network connection can be used to enable network printing of diagnostic reports, remote access to view patient diagnostic reports, and remote access to perform system diagnostics. The system 1 can include a video output port (e.g., HDMI) that can be used to output video of diagnostic measurements performed by the system 2. The output video can be displayed on an external monitor for, for example, viewing by physicians or users. The output video can also be recorded for, for example, archival purposes. The system 2 can include one or more data output ports (e.g., USB) to enable export of patient diagnostic reports to, for example, a data storage device or a computer readable medium, for example a non-volatile computer readable medium, coupled to a laser cataract surgery device for use of the diagnostic measurements in conducting laser cataract surgeries. The diagnostic reports stored on the data storage device or computer readable medium can then be accessed at a later time for any suitable purpose such as, for example, printing from an external computer in the case where the user without access to network based printing or for use during cataract surgery, including laser cataract surgery.

Figure 2:
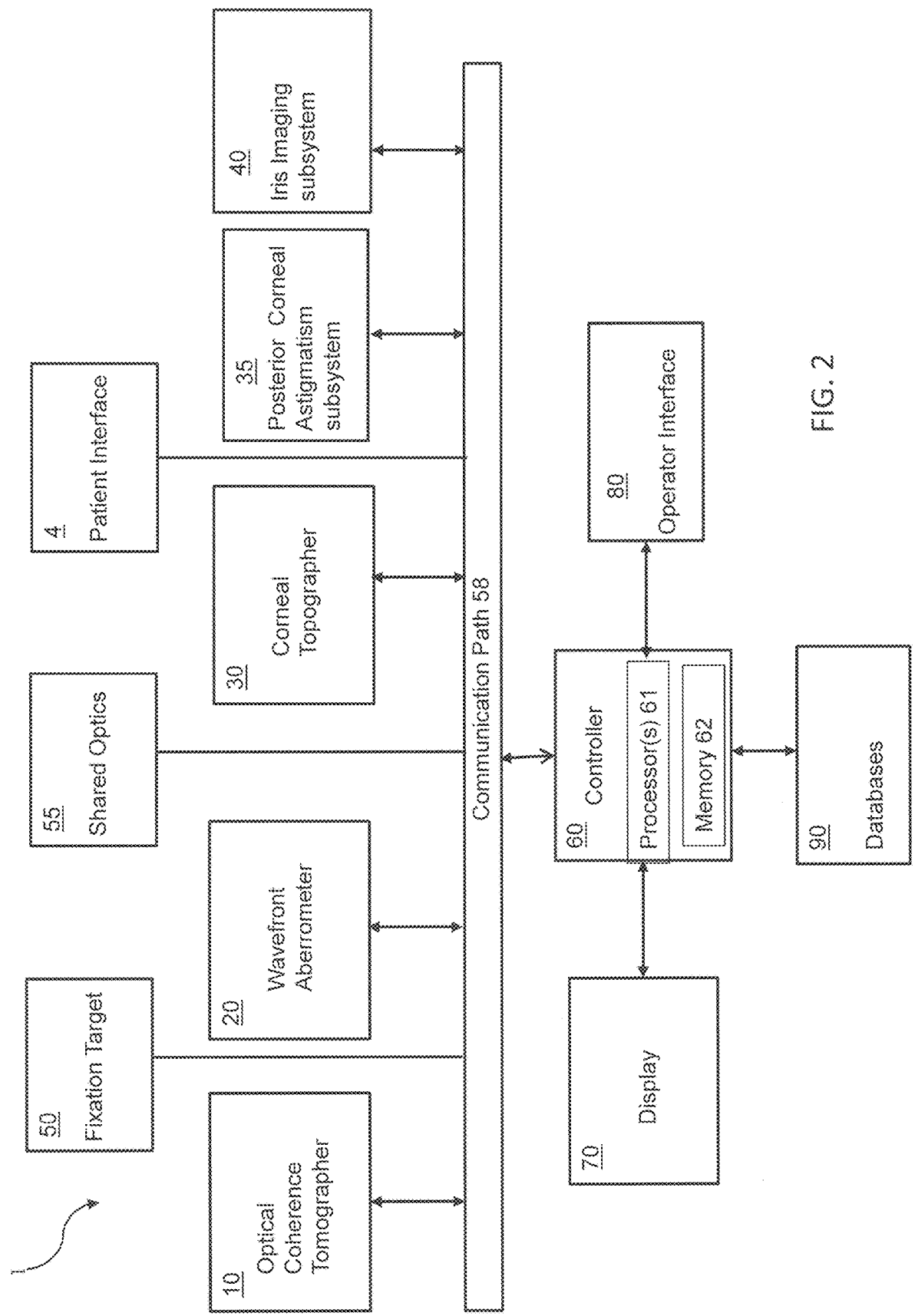
FIG. 2 is a block diagram of a system including an optical measurement instrument, and a position of an eye relative to the system according to one or more embodiments described herein which may be used by the optical measurement.

FIG. 2 is a block diagram of a system including an optical measurement instrument 1 according to one or more embodiments described herein. Optical measurement instrument 1 includes: an optical coherence tomographer (OCT) subsystem 10, a wavefront aberrometer subsystem 20, and a corneal topographer subsystem 30 for measuring one or more characteristics of a subject's eye. Optical measurement instrument 1 may further include an iris imaging subsystem 40, a fixation target subsystem 50, a controller 60, including one or more processor(s) 61 and memory 62, a display 70 and an operator interface 80. Optical measurement instrument 1 further includes a patient interface 4 for a subject to present his or her eye for measurement by optical measurement instrument 1.

The optical coherence tomography subsystem 10 is configured to measure the spatial disposition (e.g., three-dimensional coordinates such as X, Y, and Z of points on boundaries) of eye structures in three dimensions. Such structure of interest can include, for example, the anterior surface of the cornea, the posterior surface of the cornea, the anterior portion of the lens capsule, the posterior portion of the lens capsule, the anterior surface of the crystalline lens, the posterior surface of the crystalline lens, the iris, the pupil, the limbus and/or the retina. The spatial disposition of the structures of interest and/or of suitable matching geometric modeling such as surfaces and curves can be generated and/or used by the controller for a number of purposes, including, in some embodiment to program and control a subsequent laser-assisted surgical procedure. The spatial disposition of the structures of interest and/or of suitable matching geometric modeling can also be used to determine a wide variety of parameters.

As a non-limiting example, the system 1 can be configured to use a swept source OCT imaging system employing wavelengths of around 1060 nm with an 8 mm scan depth. The spatial disposition of the eye structures using optical coherence tomography should generally be measured while the patient is engaged with patient interface 4. The OCT scan depth is preferably between 8 and 50 mm, and the scan depth is preferably greater than about 24 mm or even 30 mm to achieve a full eyescan depth. The swept source wavelengths can be centered at wavelengths from 840 nm to 1310 nm. Optical coherence tomographer subsystem 10 is only one example of an eye structure imaging subsystem which may be employed in optical measurement instrument 1. In other embodiments, a different eye structure imaging subsystem may be employed, for example a Scheimpflug imager, a fluorescence imager, a structured lighting imager, a wavefront tomographer, an ultrasound imager, and a plenoptic imager.

The wavefront aberrometer subsystem 20 is configured to measure ocular aberrations, preferably including low and high order aberrations, by measuring the wavefront emerging from the eye by, for example a Shack Hartman sensor The corneal topographer subsystem 30 may apply any number of modalities to measure the shape of the cornea including one or more of a keratometry reading of the eye, a corneal topography of the eye, an optical coherence tomography of the eye, a Placido style disc topography of the eye, a reflection of a plurality of points from the corneal topography of the eye, a grid reflected from the cornea of the eye topography, a Hartmann-Shack measurement of the eye, a Scheimpflug image topography of the eye, a confocal tomography of the eye, a Helmholtz source topographer, or a low coherence reflectometry of the eye. The shape of the cornea should generally be measured while the patient is engaged with patient interface 4.

Fixation target system 50 is configured to control the patient's accommodation, because it is often desired to measure the refraction and wavefront aberrations when eye 101 is focused at its far point Images captured by the corneal topographer subsystem 10, the wavefront aberrometer 20, the optical coherence tomographer subsystem 30 or the camera 40 may be displayed with a display of the operator interface 80 of the optical measurement system 2 or the display 70 of the optical measurement system, respectively. The operator interface may also be used to modify, distort, or transform any of the displayed images.

The shared optics 55 provide a common propagation path that is disposed between the patient interface 4 and each of the optical coherence tomographer (OCT) subsystem 10, the wavefront aberrometer subsystem 20, the corneal topographer subsystem 30, and in some embodiments, an optional posterior corneal astigmatism subsystem 35, an iris imaging subsystem 40, and a fixation target subsystem 50. In many embodiments, the shared optics 55 may comprise a number of optical elements, including mirrors, lenses and beam combiners to receive the emission from the respective subsystem to the patient's eye and, in some cases, to redirect the emission from a patient's eye along the common propagation path to an appropriate director.

The controller 60 controls the operation of the optical measurement instrument 1 and can receive input from any of the optical coherence tomographer (OCT) subsystem 10, the wavefront aberrometer subsystem 20, the corneal topographer subsystem 30 for measuring one or more characteristics of the cornea of a subject's eye, the optional posterior corneal astigmatism subsystem, the iris imaging subsystem 40, the fixation target 50, the display 70 and the operator interface 80 via the communication paths 58. The controller 60 can include any suitable components, such as one or more processor, one or more field-programmable gate array (FPGA), and one or more memory storage devices. In many embodiments, the controller 60 controls the display 70 to provide for user control over the laser eye surgery procedure for pre-cataract procedure planning according to user specified treatment parameters as well as to provide user control over the laser eye surgery procedure. The communication paths 58 can be implemented in any suitable configuration, including any suitable shared or dedicated communication paths between the controller 60 and the respective system components.

The operator interface 80 can include any suitable user input device suitable to provide user input to the controller 60. For example, the user interface devices 80 can include devices such as joystick 8, a keyboard or a touchscreen display 70.

Figure 3A:
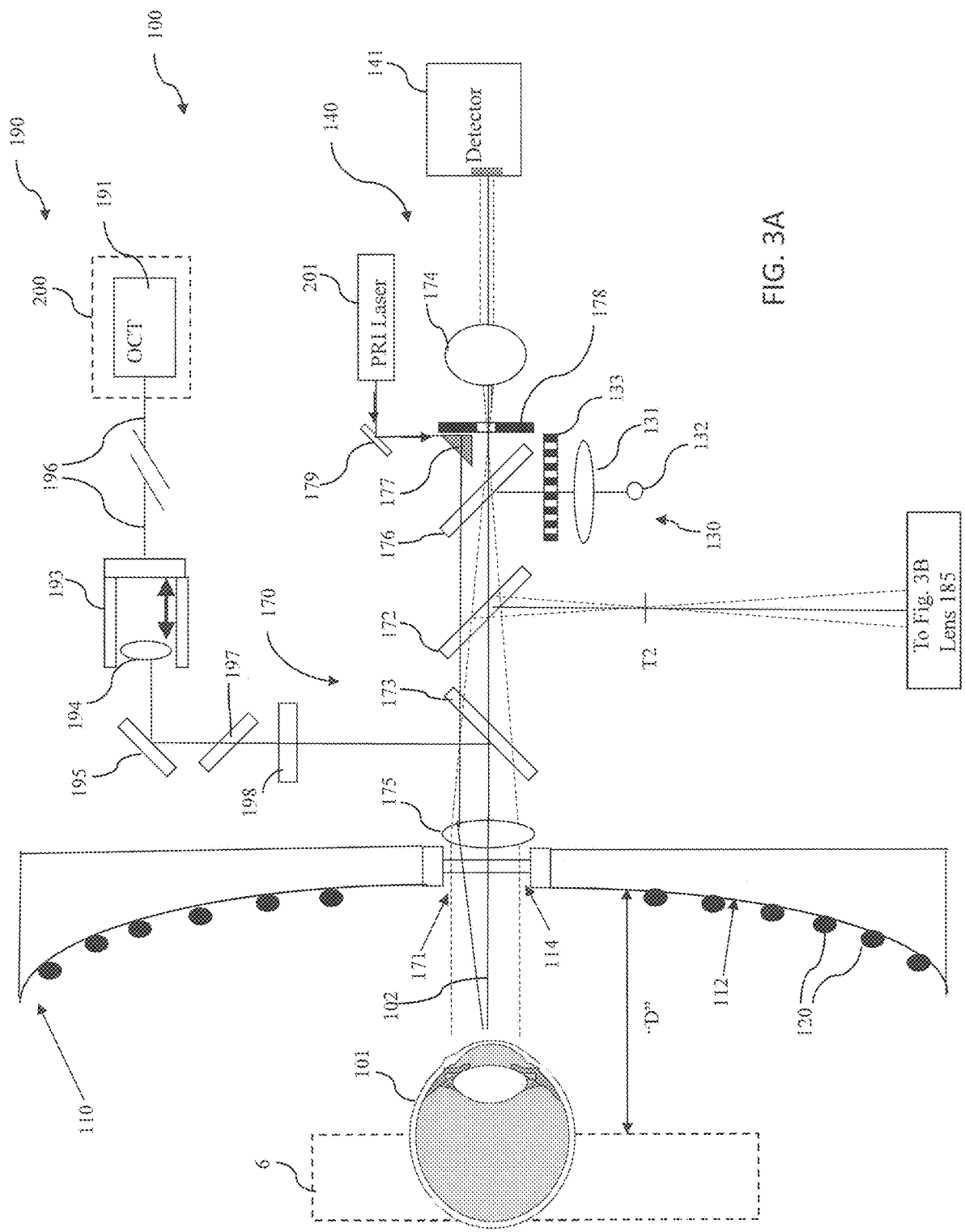
FIGS. 3A and 3B illustrate together an assembly illustrating a suitable configuration and integration of an optical coherence tomographer subsystem, a wavefront aberrometer subsystem, a corneal topographer subsystem, an iris imaging subsystem, a fixation target subsystem according to a non-limiting embodiment of the present invention.
Figure 3B:
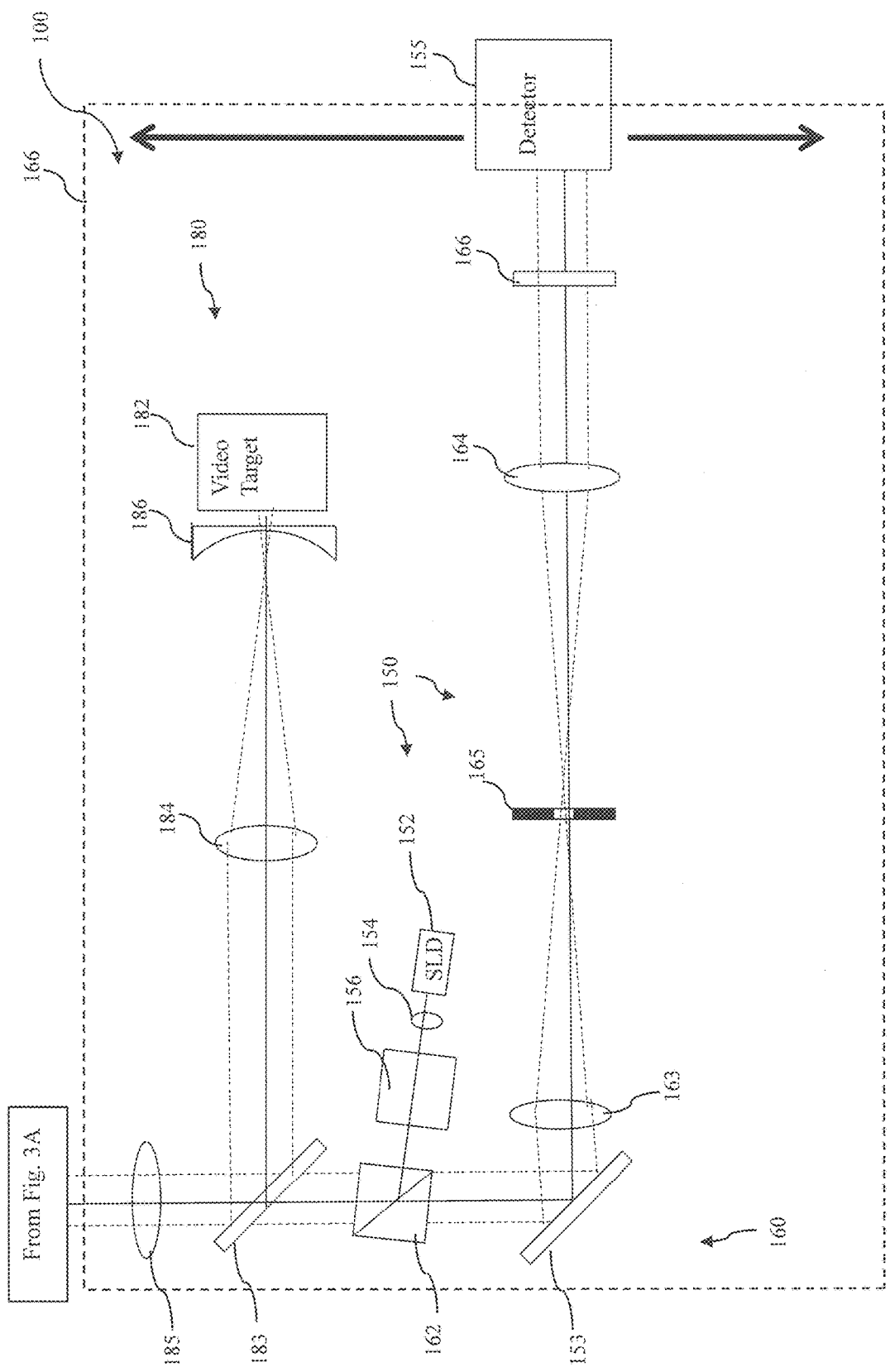

FIGS. 3A and 3B are simplified block diagrams illustrating an assembly 100 according to many embodiments, which can be included in the system 1. The assembly 100 is a non-limiting example of suitable configurations and integration of the optical coherence tomographer (OCT) subsystem 190, the wavefront aberrometer subsystem 150, the corneal topographer subsystem 140 for measuring one or more characteristics of a subject's eye, an iris imaging subsystem 40, the fixation target subsystem 180 and the shared optics.

The shared optics generally comprise one or more components of a first optical system 170 disposed along a central axis 102 passing through the opening or aperture 114 of the structure 110. A first optical system 170 directs light from the various light sources along the central axis 102 towards the eye and establishes a shared or common optical path along which the light from the various light sources travel to the eye 101. In one embodiment, optical system 170 comprises a quarter wave plate 171, a first beamsplitter 172, a second beamsplitter 173, an optical element (e.g., a lens) 174, a second lens 175, a third beamsplitter 176, and a structure including an aperture 178. Additional optical systems may be used in assembly 100 to direct light beams from one or more light sources to the first optical system 170. For example, a second optical system 160 directs light to the first optical system 170 from the wavefront aberrometer subsystem 150 and comprises mirror 153, beam splitter 162 and beam splitter 183, and lens 185.

Other embodiments of suitable systems for the measurement of refractive error, and particularly to methods and techniques for compiling a top put graphic mapping of refractive errors include: U.S. Pat. No. 6,550,917, filed Oct. 20, 2000, entitled "Dynamic Range Extension Techniques For A Wavefront Sensor Including Use In Ophthalmic Measurement"; U.S. Pat. No. 6,908,196, filed Feb. 21, 2003, entitled "System And Method For Performing Optical Corrective Procedures With Real-Time Feedback"; U.S. Pat. No. 7,455,407, filed Apr. 21, 2004, entitled "System And Method Of Measuring And Mapping Three Dimensional Structures"; U.S. Pat. No. 7,553,022, filed Jul. 27, 2007, entitled "System And Method Of Measuring And Mapping Three Dimensional Structures"; U.S. Pat. No. 7,988,292, filed May 29, 2009, entitled "System And Method Of Measuring And Mapping Three Dimensional Structures"; and WO2001/058339, filed Feb. 8, 2001, entitled "Dynamic Range Extension Techniques For A Wavefront Sensor." These references are hereby incorporated herein by reference in their entirety as if fully set forth.

Other configurations of the assembly 100, such as liquid lens configurations, may be possible and may be apparent to a person of skill in the art.

The corneal topographer subsystem 140 comprises a structure 110 having a principal surface 112 with an opening or aperture 114 therein; a plurality of first (or peripheral) light sources 120 provided on the principal surface 112 of the structure 110; a Helmholz light source 130; and a detector, photodetector, or detector array 141.

In one embodiment, structure 110 has the shape of an elongated oval or "zeppelin" with openings or apertures at either end thereof. An example of such a structure is disclosed in Yobani Meji'a-Barbosa et al., "Object surface for applying a modified Hartmann test to measure corneal topography," APPLIED OPTICS, Vol. 40, No. 31 (Nov. 1, 2001) ("Meji'a-Barbosa"). In some embodiments, principal surface 112 of structure 110 is concave when viewed from the cornea of eye 101, as illustrated in FIG. 1A.

In one embodiment, where principal surface 112 is concave, principal surface 112 has the shape of a conical frustum. Alternatively, principal surface 112 may have a shape of hemisphere or some other portion of a sphere, with an opening or aperture therein. Also alternatively, principal surface 112 may have the shape of a modified sphere or conical frustum, with a side portion removed. Beneficially, such an arrangement may improve the ergonomics of assembly 100 by more easily allowing structure 110 to be more closely located to a subject's eye 101 without being obstructed by the subject's nose. Of course, a variety of other configurations and shapes for principal surface 112 are possible.

In the embodiment of FIG. 1A, the plurality of first light sources 120 are provided on the principal surface 112 of structure 110 so as to illuminate the cornea of eye 101. In one embodiment, light sources 122 may comprise individual light generating elements or lamps, such as light emitting diodes (LEDs) and/or the tips of the individual optical fibers of a fiber bundle. Alternatively, principal surface 112 of structure 110 may have a plurality of holes or apertures therein, and one or more backlight lamps, which may include reflectors and/or diffusers, may be provided for passing lighting through the holes to form the plurality of first light sources 120 which project light onto the cornea of eye 101. Other arrangements are possible.

Other embodiments of suitable systems include: U.S. Pat. No. 8,126,246, filed Jan. 8, 2009, entitled "Systems And Methods For Measuring Surface Shape"; U.S. Pat. No. 8,260,024, filed Jan. 23, 2012, entitled "Systems And Methods For Measuring Surface Shape"; and European Patent Application No. 20090701204, filed Jan. 8, 2008, entitled "Systems And Methods For Measuring Surface Shape." These references are hereby incorporated herein by reference in their entirety as if fully set forth.

In another embodiment, structure 110 is omitted from assembly 100, and the first light sources 120 may be independently suspended (e.g., as separate optical fibers) to form a group of first light sources 120 arranged around a central axis, the group being separated from the axis by a radial distance defining an aperture in the group (corresponding generally to the aperture 114 in the structure 110 illustrated in FIG. 1A).

In operation, a ray (solid line) from one of the first light sources 120 is reflected by the cornea and passes through optical system 170 (including aperture 178) to appear as a light spot on detector array 141. It will be appreciated that this ray is representative of a small bundle of rays that make it through optical system 170 and onto detector array 141, all of which will focus to substantially the same location on detector array 141. Other rays from that first light source 120 are either blocked by the aperture 178 or are otherwise scattered so as to not pass through the optical system 170. In similar fashion, light from the other first light sources 120 are imaged onto detector array 141 such that each one of first light sources 120 is imaged or mapped to a location on detector array 141 that may be correlated to a particular reflection location on the cornea of eye 101 and/or the shape of the cornea. Thus, detector array 141 detects the light spots projected thereon and provides corresponding output signals to a processor of controller 60 (FIG. 2). The processor determines the locations and/or shape of the light spots on detector array 141, and compares these locations and/or shapes to those expected for a standard or model cornea, thereby allowing the processor of controller 60 to determine the corneal topography. Alternatively, other ways of processing the spot images on detector array 141 may be used to determine the corneal topography of eye 101, or other information related to the characterization of eye 101.

Detector array 141 comprises a plurality of light detecting elements arranged in a two dimensional array. In one embodiment, detector array 141 comprises such a charge-coupled device (CCD), such as may be found in a video camera. However, other arrangements such as a CMOS array, or another electronic photosensitive device, may be employed instead. Beneficially, the video output signal(s) of detector array 141 are provided to processor 61 which processes these output signals as described in greater detail below.

Assembly 100 also comprises a Helmholtz light source 130 configured according to the Helmholtz principle. As used herein, the term "Helmholtz source" or "Helmholtz light source" means one or a plurality of individual light sources disposed such that light from each of the individual light sources passes through an optical element having optical power, reflects off of a reference or test object, passes through the optical element, and is received by a detector, wherein light from the Helmholtz source is used to determine geometric and/or optical information of at least a portion of a surface of the reference or test object. In general, it is a characteristic of Helmholtz sources that the signal at the detector is independent of the relative position of the test or reference object relative to the Helmholtz source. As used herein, the term "optical element" means an element that refracts, reflects, and/or diffracts light and has either positive or negative optical power.

In such embodiments, the Helmholtz light source 130 is located at optical infinity with respect to eye 101. The Helmholtz principle includes the use of such infinite sources in combination with a telecentric detector system: i.e., a system that places the detector array at optical infinity with respect to the surface under measurement, in addition to insuring that the principal measured ray leaving the surface is parallel to the optical axis of the instrument. The Helmholtz corneal measurement principle has the Helmholtz light source at optical infinity and the telecentric observing system so that detector array 141 is also optically at an infinite distance from the images of the sources formed by the cornea. Such a measurement system is insensitive to axial misalignment of the corneal surface with respect to the instrument.

In one embodiment, the Helmholtz light source 130 comprises a second light source 132 which may comprise a plurality of lamps, such as LEDs or optical fiber tips. In one embodiment, second light source 132 comprises an LED and a plate 133 with plurality of holes or apertures in a surface that are illuminated by one or more backlight lamps with an optical element 131, which may comprise diffusers.

In one embodiment, second light sources 132 are located off the central optical axis 102 of assembly 100, and light from second light sources 132 is directed toward optical element 171 by third beamsplitter 176.

The operation of the topographer portion of system 100 may be conducted with the combined use of first light source 120 and the Helmholz light source 130. In operation, detector array 141 detects the light spots projected thereon from both Helmholz light source 130 (detected at a central portion of detector array 141) and first light sources 120 (detected at a peripheral portion of detector array 141) and provides corresponding output signals to processor. In general, the images of first light sources 120 that appear on detector array 140 emanate from an outer region of the surface of the cornea, and the images of Helmholz light source 130 that appear on detector array 141 emanate from a central or paraxial region of the surface of the cornea. Accordingly, even though information about the central region of the corneal surface (e.g., surface curvature) cannot be determined from the images of first light sources 120 on detector array 141, such information can be determined from the images of Helmholz light source 130 on detector array 141. A processor of controller 60 determines the locations and/or shapes of the light spots on detector array 141, and compares these locations and/or shapes to those expected based for a standard or model cornea, thereby allowing the processor to determine the corneal topography of eye 101. Accordingly, the topography of the entire corneal surface can be characterized by system 100 without a "hole" or missing data from the central corneal region.

A fourth light source 201 off the central axis 102 may be directed along optical axis 102 by mirrors 177, 179 disposed on or near the aperture 178, perpendicular to the optical axis 102 are configured as a pupil retroreflection illuminator. The pupil retroreflecton illuminator is configured to direct a disc of light toward a patient's eye, whereby the disc of light may be reflected from reflective surfaces within the eye, and the reflected light is transmitted by optical path 170 to detector 141. The pupil retroreflection illuminators may optionally be configured such that, when a patient's pupil is dilated, the disc of light from light source 201 is reflected from an implanted IOL to image the IOL, including any fiducial marks; if IOL is imperfectly placed, detector 141 may be used to determine IOL edges are decentered. Also, images from detector 141 using the pupil retroreflection illuminator may see folds, for instance, unfolded edge if the IOL did not unfold properly.

The wavefront aberrometer subsystem 150 of the assembly 100 comprises a third light source 152 providing a probe beam and a wavefront sensor 155. The wavefront aberrometer subsystem 150 preferably further comprises a collimating lens 154, a polarizing beamsplitter 156, an adjustable telescope comprising a first optical element, lens 163 and a second optical element, lens 164, a movable stage or platform 166, and a dynamic-range limiting aperture 165 for limiting a dynamic range of light provided to wavefront sensor 155 so as to preclude data ambiguity. Light from the wavefront aberrometer subsystem is directed to one of the constituent optical elements of the optical system 170 disposed along a central axis 102 passing through the opening or aperture 114 of the structure 110. It will be appreciated by those of skill in the art that the lenses 163, 164, or any of the other lenses discussed herein, may be replaced or supplemented by another type of converging or diverging optical element, such as a diffractive optical element.

Light source 152 is preferably an 840 nm SLD (super luminescent laser diode). An SLD is similar to a laser in that the light originates from a very small emitter area. However, unlike a laser, the spectral width of the SLD is very broad, about 40 nm. This tends to reduce speckle effects and improve the images that are used for wavefront measurements.

Preferably, wavefront sensor 155 is a Shack-Hartmann wavefront sensor comprising a detector array and a plurality of lenslets for focusing received light onto its detector array. In that case, the detector array may be a CCD, a CMOS array, or another electronic photosensitive device. However, other wavefront sensors may be employed instead. Embodiments of wavefront sensors which may be employed in one or more systems described herein are described in U.S. Pat. No. 6,550,917, issued to Neal et al. on Apr. 22, 2003, and U.S. Pat. No. 5,777,719, issued to Williams et al. on Jul. 7, 1998, both of which patents are hereby incorporated herein by reference in their entirety.

The aperture or opening in the middle of the group of first light sources 120 (e.g., aperture 114 in principal surface 112 of structure 110) allows system 100 to provide a probe beam into eye 101 to characterize its total ocular aberrations. Accordingly, third light source 152 supplies a probe beam through a light source polarizing beam splitter 156 and polarizing beam splitter 162 to first beamsplitter 172 of optical system 170. First beamsplitter 172 directs the probe beam through aperture 114 to eye 101. Preferably, light from the probe beam is scattered from the retina of eye 101, and at least a portion of the scattered light passes back through aperture 114 to first beamsplitter 172. First beamsplitter 172 directs the back scattered light back through beam splitter 172 to polarizing beamsplitter 162, mirror 153, to wavefront sensor 155.

Wavefront sensor 155 outputs signals to a processor of controller 60 which uses the signals to determine ocular aberrations of eye 101. Preferably, processor 141 is able to better characterize eye 101 by considering the corneal topography of eye 101 measured by the Corneal Topography Subsystem, which may also be determined by processor 141 based on outputs of detector array 141, as explained above.

In operation of the wavefront aberrometer subsystem 150, light from light source 152 is collimated by lens 154. The light passes through light source polarizing beam splitter 156. The light entering light source polarizing beam splitter 156 is partially polarized. Light source polarizing beam splitter 156 reflects light having a first, S, polarization, and transmits light having a second, P, polarization so the exiting light is 100% linearly polarized. In this case, S and P refer to polarization directions relative to the hypotenuse in light source polarizing beam splitter 156.

Light from light source polarizing beam splitter 156 enters polarizing beamsplitter 162. The hypotenuse of polarizing beamsplitter 162 is rotated 90 degrees relative to the hypotenuse of light source polarizing beamsplitter 156 so the light is now S polarized relative the hypotenuse of polarizing beamsplitter 162 and therefore the light reflects upwards. The light from polarizing beamsplitter 162 travels upward and passes through toward beam splitter 172, retaining its S polarization, and then travels through quarter wave plate 171. Quarter wave plate 171 converts the light to circular polarization. The light then travels through aperture 114 in principal surface 112 of structure 110 to eye 101. Preferably, the beam diameter on the cornea is between 1 and 2 mm. Then, the light travels through the cornea and focuses onto the retina of eye 101.

The focused spot of light becomes a light source that is used to characterize eye 101 with wavefront sensor 155. Light from the probe beam that impinges on the retina of eye 101 scatters in various directions. Some of the light reflects back as a semi-collimated beam back towards assembly 100. Upon scattering, about 90% of the light retains its polarization. So the light traveling back towards assembly is substantially still circularly polarized. The light then travels through aperture 114 in principal surface 112 of structure 110, through quarterwave plate 171, and is converted back to linear polarization. Quarterwave plate 171 converts the polarization of the light from the eye's retina so that it is P polarized, in contrast to probe beam received from third light source 150 having the S polarization. This P polarized light then reflects off of first beamsplitter 172, and then reaches polarizing beamsplitter 162. Since the light is now P polarized relative the hypotenuse of polarizing beamsplitter 162, the beam is transmitted and then continues onto mirror 153. After being reflected by mirror 153, light is sent to an adjustable telescope comprising a first optical element 164 and a second optical element (e.g., lens) 163 and a movable stage or platform 166. The beam is also directed through a dynamic-range limiting aperture 165 for limiting a dynamic range of light provided to wavefront sensor 155 so as to preclude data ambiguity.

When wavefront sensor 155 is a Shack-Hartmann sensor, the light is collected by the lenslet array in wavefront sensor 155 and an image of spots appears on the detector array (e.g., CCD) in wavefront sensor 155. This image is then provided to a process of the controller 60 and analyzed to compute the refraction and aberrations of eye 101.

An OCT subsystem 190 of assembly 100 preferably comprises an OCT assembly 191, and a third optical path 192 which directs the OCT beam of the OCT light source to the first optical path 170. The third optical path 192 preferably comprises a fiber optic line 196, for conducting the OCT beam from the OCT light source, a z-scan device 193 operable to alter the focus of the beam in the z-direction (i.e., along the direction of propagation of the OCT beam) under control of the controller, and x-scan device 195, and a y-scan device 197 operable to translate the OCT beam in the x and y directions (i.e., perpendicular to the direction of propagation of the of the OCT beam), respectively, under control of the controller. A first set 198 of polarization controllers may optionally be included to change a polarization property of the OCT light source. The OCT light source and reference arm may be incorporated into the main unit 4 of the optical measurement instrument 1 shown in FIG. 1A. Alternatively, the OCT assembly 191 may be housed in a second unit 200 and the OCT beam from the OCT source may be directed from the second housing 200 to the main unit by optical pathway 192.

The OCT systems and methods of the present invention are preferably FD-OCT (Fourier domain optical coherence tomography) systems, including either an SD-OCT (spectral domain optical coherence tomography) system or, more preferably, an SS-OCT (swept source optical coherence tomography) system. In conventional FD-OCT systems, the interference signal is distributed and integrated over numerous spectral wavelength intervals, and is inverse Fourier transformed to obtain the depth-dependent reflectivity profile of the sample. The profile of scattering as a function of depth is referred to as an A-scan (Axial-scan). The beam can be scanned laterally to produce a set of A-scans that can be combined together to form a tomogram of the sample (a B-scan).

In an SD-OCT system, various spectral wavelength intervals of the combined returned light from the reference and sample arms are spatially encoded using, for instance, a collimator, diffraction grating, and a linear detector array. Resampling of the data obtained from the linear detector array is performed in order to correct for the nonlinear spatial mapping of wavenumbers. After resampling and subtraction of the dc background, the depth profile structural information is obtained by performing the inverse Fourier transform operation. In swept-source OCT, the broad bandwidth optical source is replaced by a rapid-scanning laser source. By rapidly sweeping the source wavelength over a broad wavelength range, and collecting all the scattering information at each wavelength and at each position, the composition of the collected signal is equivalent to the spectral-domain OCT technique. The collected spectral data is then inverse Fourier transformed to recover the spatial depth-dependent information.

FD-OCT suffers from an inherent sample-independent limited depth range, typically between 1 and 5 mm. One limitation flows from the fact that FD-OCT extracts depth information from the inverse Fourier transform of a spectral interferogram. Since the spectral interferogram can only be recorded as a real signal, its Fourier transform is necessarily Hermitian symmetric about the zero path length difference (ZPD) position. As a result, the positive and negative displacements about the ZPD cannot be unambiguously resolved, which gives rise to mirror image artifacts and generally halves the useable range. This is referred to as the complex conjugate ambiguity. Another limitation is a sensitivity fall-off which results in reduced sensitivity with increasing depth. Moreover, since the signal in OCT is derived only from backscattered photons, optical attenuation from absorption and scattering generally result in a useable imaging depth of about 1-4 mm.

Several "full range" OCT techniques have been developed that eliminate the complex conjugate artifacts to effectively double the measurement range around the ZPD position. These full range OCT techniques result in useable imaging depths of up to about 5 mm or even up to about 8 mm. Suitable full range techniques include methods that dither the reference leg length (M. Wijtkowski, et al, Opt. Lett. V27, #16, pg 1415, 2002), or that exploit phase dispersion compensation (Kottig, et al, Opt. Express V20, #22, pg 24925, 2012) to break the phase ambiguity.

Figure 4:
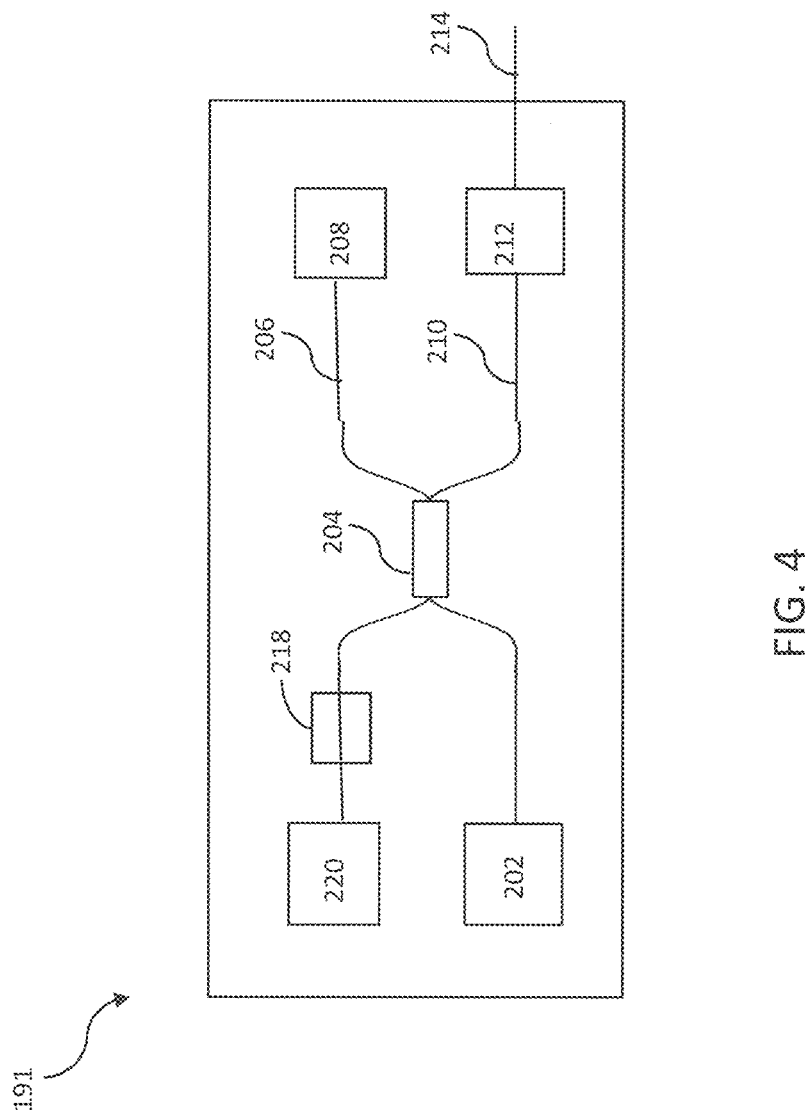
FIG. 4 is a block diagram of an OCT assembly according to many embodiments of the present invention.

As shown in FIG. 4, the OCT assembly 191 of OCT subsystem 190 includes a broadband or a swept light source 202 that is split by a coupler 204 into a reference arm 206 and a sample arm 210. The reference arm 206 includes a module 208 containing a reference reflection along with suitable dispersion and path length compensation. The sample arm 210 of the OCT assembly 191 has an output connector 212 that serves as an interface to the rest of the optical measurement instrument. The return signals from both the reference and sample arms 206, 210 are then directed by coupler 204 to a detection device 220, which employs one of time domain, frequency, or single point detection techniques. In FIG. 4, a swept source technique is used with a laser wavelength of 1060 nm swept over a range of 8-50 mm depth. A second set 218 of polarization controllers may be used to change a polarization property of the reference beam of the reference arm.

FIG. 5 is a schematic drawing of a human eye 400. In many embodiments, a light beam 401 from a light source enters the eye from the left of FIG. 5, refracts into the cornea 410, passes through the anterior chamber 404, the iris 406 through the pupil, and reaches lens 402. After refracting into the lens, light passes through the vitreous chamber 412, and strikes the retina 476, which detects the light and converts it to an electric signal transmitted through the optic nerve to the brain (not shown). The vitreous chamber 412 contains the vitreous humor, a clear liquid disposed between the lens 402 and retina 476. As indicated in FIG. 5, cornea 410 has corneal thickness (CT), here considered as the distance between the anterior and posterior surfaces of the cornea. Anterior chamber 404 has anterior chamber depth (ACD), which is the distance between the anterior surface of the cornea and the anterior surface of the lens. Lens 402 has lens thickness (LT) which is the distance between the anterior and posterior surfaces of the lens. The eye has an axial length (AXL) which is the distance between the anterior surface of the cornea and the retina 476. FIG. 5 also illustrates that, in many subjects the lens, including the lens capsule, may be tilted at one or more angles relative to the optical axis, including an angle $\gamma$ relative to the optical axis of the eye.

The optical system may also be arranged so that the movement pattern of the scan mirrors provides a lateral motion across the retina so that the shape of the retina may be determined. It is of particular interest to measure the shape and location of the depressed region of the retina named the foveal pit. When the patient is looking directly into the instrument, with their line of sight aligned to the fixation target, the foveal pit will be in center of the OCT lateral scan. This information is beneficial in that it informs the instrument operator if the patient was looking directly at the target when the measurement was made. Retinal scans are also useful in detecting disease conditions. In some cases, there may be an absence of a foveal pit that also is considered an indication of a corneal abnormality.

The average axial length of the adult human eye is about 24 mm. Since the full range imaging depth of the OCT measurements are only about 5 mm to 8 mm, then OCT scanning of the invention may provide for OCT scans at different depths of the eye that can be combined together to form a combined OCT image of the eye. The OCT measurements of the present invention preferably includes OCT imaging at various depths of the patient's eye for imaging 1) at least a portion of the retina, 2) at least a portion of the anterior portion of the eye, including at least a portion of the cornea (anterior and posterior), iris, and lens (anterior and posterior), and 3) performing axial eye length measurements. In a preferred embodiment, the coherence depth range of the OCT system to exceed the length of the eye so that the entire length of the eye may be measured at one time without the need to combine different depth ranges. In that case, however, it may still be beneficial to change the focus of the beam entering into the eye so that the strength of the captured light may be optimized for resolving different regions of the eye. For example, the beam may be focused on the anterior portion of the eye for increased resolution in that region while simultaneously a measurement of the length of the whole eye is being made. Similarly, the beam may be focused on the retina for high resolution measurements in that section while simultaneously the whole eye length is being measured. For both situations, the scan geometry may be arranged so that while the beam is scanning across on region, the beam is substantially stationary on the other region so that even though the beam is defocused there, the return signal strength from the defocus region is sufficient to provide a strong signal.

Figure 6A:
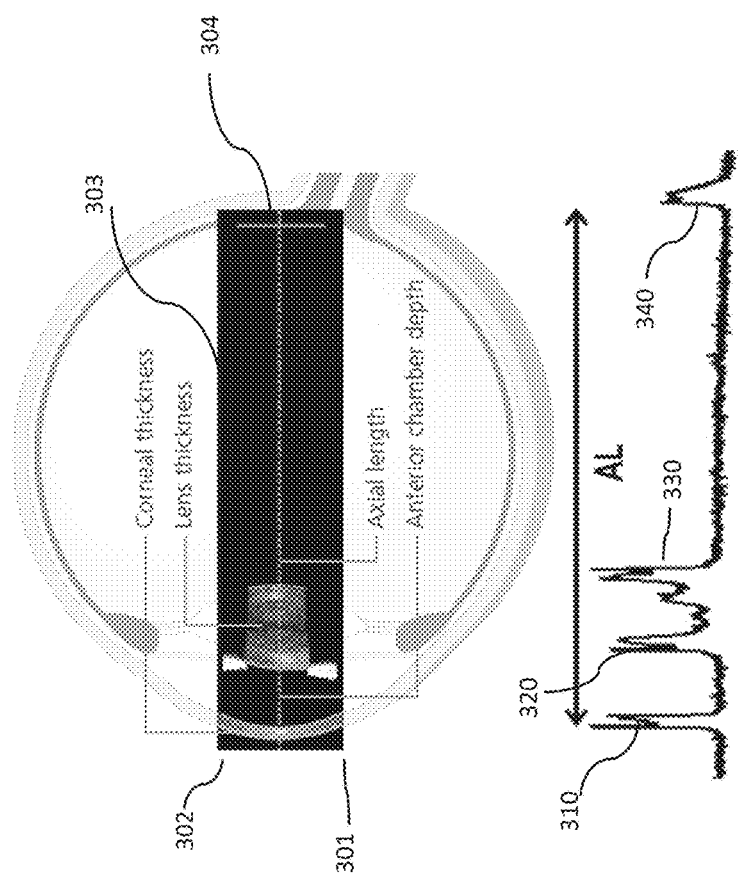
FIG. 6A illustrates a preferred scanning region for the OCT subsystem according to many embodiments of the present invention.
Figure 6B:
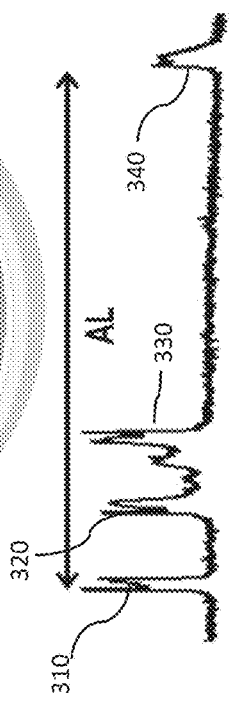
FIG. 6B shows a representative graph of an intensity of an OCT signal of an OCT subsystem 190 according to many embodiments as a function of depth along the axis defining the axial length of the eye.
Figure 6C:
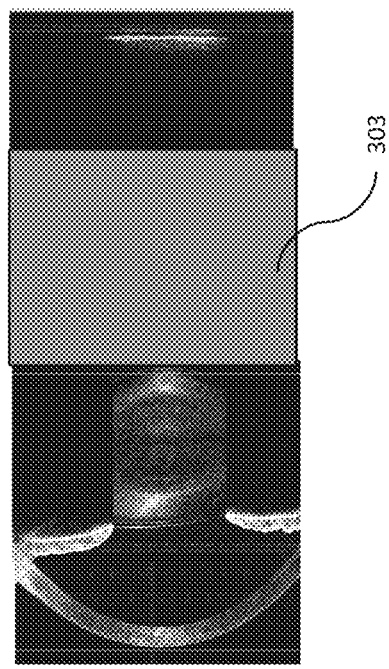
FIG. 6C shows a cross-section of an eye obtained by an optical measurement system of the present invention using an OCT subsystem according to the present invention

FIGS. 6A-6C illustrate various aspects of the OCT subsystem 190 according to various aspects of the present invention. FIG. 6A illustrates a preferred scanning region for the OCT subsystem according to many embodiments of the present invention. The scanning region may be defined from starting point 301 to ending point 302 at the anterior portion of the eye extending in a direction transverse the direction of propagation of the OCT beam and also extending in a direction parallel to an axis defining the axial length of the eye to the posterior portion 304 of the eye. The lateral scanning region should generally be sufficiently large in the lateral direction to permit imaging of the central portion of the cornea, at least a portion of the iris, at least a portion of the lens and at least of the retina. It should be noted that a region 303 between the posterior portion of the lens and the surface of the retina may optionally not be scanned by OCT subsystem 190 because the portion 330 does not contain anatomical structure for 3D analysis.

FIG. 6B shows a representative graph of an intensity of an OCT signal of an OCT subsystem 190 according to many embodiments as a function of depth along the axis defining the axial length of the eye. The graph generally exhibits approximately four peaks having a complex structure: (1) a peak 310 having a doublet-like structure and generally corresponding to a location of the cornea; (2) a peak 320 having a doublet-like structure and generally corresponding to a location of an anterior surface of the lens; (3) a peak 330 having a complex structure generally corresponding to a location of a posterior surface of the lens; and (4) a peak 340 generally corresponding to a location of a retina. A distance between peak 310 and peak 340 can be used to calculate the axial length (AL) of the eye. Preferably, an OCT scan by OCT subsystem 190, including both an A-scan and B-scan, is conducted at least one location in the anterior portion of the eye (e.g., a location of a cornea, a location of an anterior surface of a lens and/or a location of a posterior surface of the lens) and at least one location in the posterior portion of the eye (e.g., at a location of a retina). In some embodiments, an OCT scan by the OCT subsystem 190, including both an A-Scan and a B-scan is performed at a location corresponding to each of a location of the cornea, a location of an anterior surface of the lens, a location of a posterior surface of the lens, and a location corresponding to a retina.

It should be noted that because the OCT subsystem 190 provides for the detection of various structures of the eye, including a location of the cornea, the OCT subsystem 190 may be used as a ranging system to precisely align the patient in relation to the optical measurement system 1 of the present invention. The use of the OCT as a ranging system can significantly improve accuracy of corneal topography measurements, including keratometry measurements, which are sensitive to misalignment of the corneal structures.

FIG. 6C shows a cross-section of an eye obtained by an optical measurement system of the present invention using an OCT subsystem according to the present invention.

Figure 7:
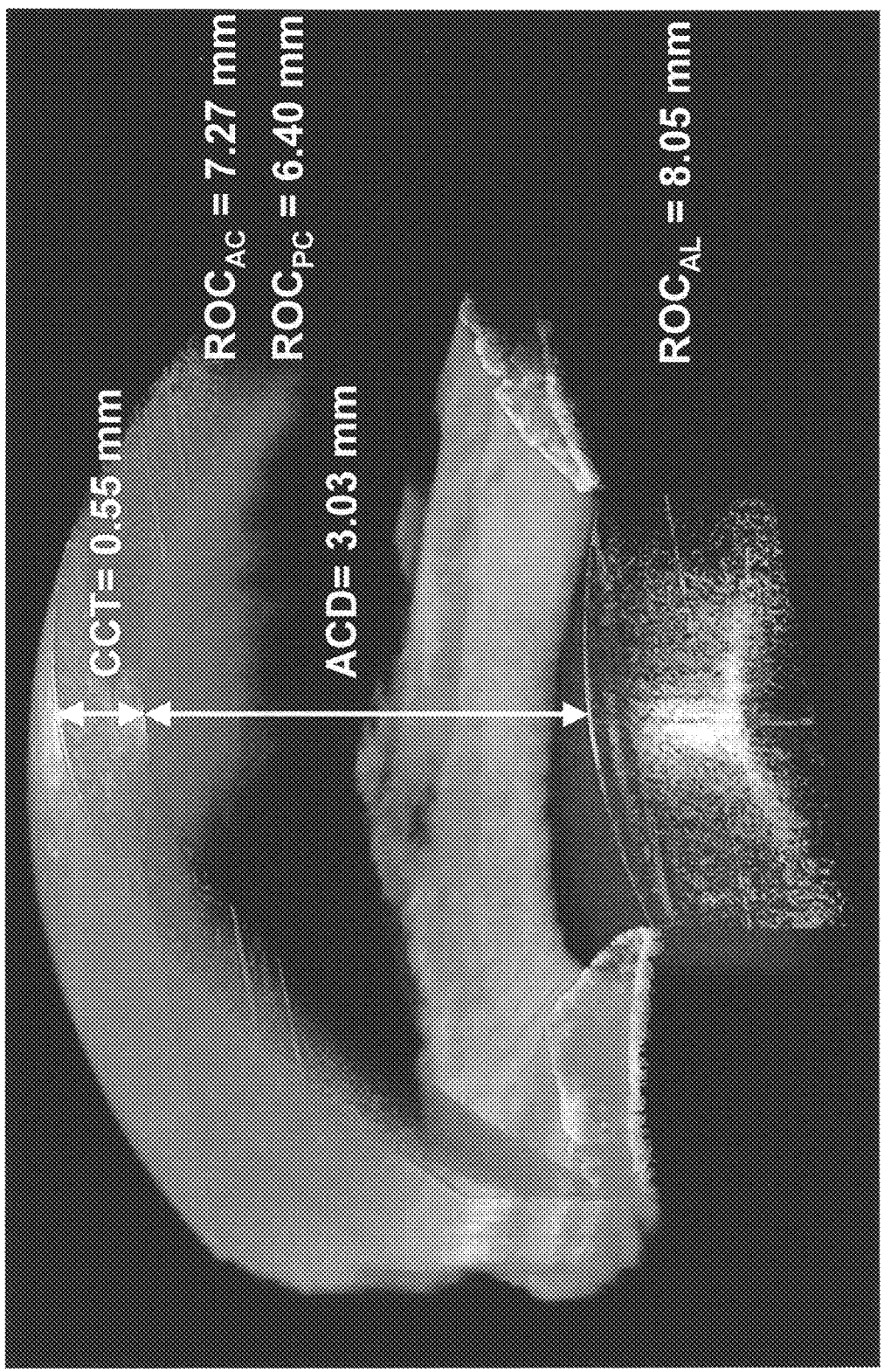
FIG. 7 is a 3-dimensional representation of an anterior portion of an eye obtained using the optical measurement system according to many embodiments.

FIG. 7 shows a 3 dimensional view of an eye obtained by an optical measurement system of the present invention using an OCT subsystem according to the present invention. FIG. 7 evidences that the OCT subsystem of the present invention is operable to obtain biometry measurements according to the present invention, including the central corneal thickness (CCT), the anterior chamber depth (ACD), the radius of curvature of the anterior cornea ($ROC_{AC}$), the radius of curvature of the Posterior cornea ($ROC_{PC}$) and the Radius of curvature of the axial length ($ROC_{AL}$).

Preferably, the OCT subsystem 190 provides sufficiently resolved structural information to provide a structural assessment that may provide a user with an indication of suitability of a particular patient for a laser cataract procedure. In one embodiment, an OCT scan performed by the OCT subsystem 190 at or near the retina (i.e., a retina scan) is sufficiently resolved to identify the foveal pit location and depth, wherein a lack of depression indicates an unhealthy retina.

In another embodiment, the optical measurement instrument 1 of the present invention provides one or more measurements sufficient to provide an assessment of the tear film of a patient. In one embodiment, the tear film assessment comprises a comparison of a wavefront aberrometry map and a corneal topography map or OCT map of the patient's eye, by, for instance, determining the irregular features in either the wavefront aberrometery or corneal topopgraphy maps This can be achieved by first fitting the surface (either wavefront or topography) to smooth functions such as Zernike or Taylor polynomials, and then subtracting this smooth surface from the original surface data. The resulting map is the residual of what does not fit a smooth surface and is highly correlated with the tear film (Haixia Liu, Larry Thibos, Carolyn G. Begley, Arthur Bradley, "MEASUREMENT OF THE TIME COURSE OF OPTICAL QUALITY AND VISUAL DETERIORATION DURING TEAR BREAK-UP," Investigative Ophthalmology & Visual Science, June 2010, Vol. 51, No. 6). A determination of whether the tear film is broken (if not smooth); an assessment of the tear film, including tear film breakup, can also be obtained by reviewing the shape of spots on the topographer. For instance, a finding or indication that the tear film is disrupted, or broken, may be based upon the shape of a spot in that, if the spots are not round, and have, for instance, an oblong or broken up shape, it indicates that tear film is disrupted. The existence of such a disrupted tear film may indicate that K value, and other ocular measurements may not be reliable. Further indications of the state of the tear film may be made by comparing the OCT and the topographer, or wavefront data (See Kob—Simultaneous Measurement of Tear Film Dynamics IOVS, July 2010, Vol. 51, No. 7).

In operation, as shown in FIG. 3A, after exiting connector 212, the OCT beam 214 is collimated, preferably using a collimating optical fiber 196. Following collimating fiber 196 the OCT beam 214 is directed to an z-scan device 193 operable to change the focal point of the OCT beam in a z-direction, and x- and y-scan devices 195 and 197, which are operable to scan the OCT beam in x and y-directions perpendicular to the z-direction.

Following the collimating optical fiber 196, the OCT beam 214 continues through a z-scan device 193, 194. Preferably, the z-scan device is a Z telescope 193, which is operable to scan focus position of the OCT beam 214 in the patient's eye 101 along the Z axis. For example, the Z-telescope can include a Galilean telescope with two lens groups (each lens group includes one or more lenses). One of the lens groups moves along the Z axis about the collimation position of the Z-telescope 193. In this way, the focus position in the patient's eye 101 moves along the Z axis. In general, there is a relationship between the motion of lens group and the motion of the focus point. The exact relationship between the motion of the lens and the motion of the focus in the z axis of the eye coordinate system does not have to be a fixed linear relationship. The motion can be nonlinear and directed via a model or a calibration from measurement or a combination of both. Alternatively, the other lens group can be moved along the Z axis to adjust the position of the focus point along the Z axis. The Z-telescope 84 functions as a z-scan device for changing the focus point of the OCT beam 214 in the patient's eye 101. The Z-scan device can be controlled automatically and dynamically by the controller 60 and selected to be independent or to interplay with the X and Y scan devices described next.

After passing through the z-scan device, the OCT beam 214 is incident upon an X-scan device 195, which is operable to scan the OCT beam 214 in the X direction, which is dominantly transverse to the Z axis and transverse to the direction of propagation of the OCT beam 214. The X-scan device 195 is controlled by the controller 60, and can include suitable components, such as a lens coupled to a MEMS device, a motor, galvanometer, or any other well-known optic moving device. The relationship of the motion of the beam as a function of the motion of the X actuator does not have to be fixed or linear. Modeling or calibrated measurement of the relationship or a combination of both can be determined and used to direct the location of the beam.

After being directed by the X-scan device 196, the OCT beam 214 is incident upon a Y scan device 197, which is operable to scan the OCT beam 214 in the Y direction, which is dominantly transverse to the X and Z axes. The Y-scan device 197 is controlled by the controller 60, and can include suitable components, such as a lens coupled to a MEMS device, motor, galvanometer, or any other well-known optic moving device. The relationship of the motion of the beam as a function of the motion of the Y actuator does not have to be fixed or linear. Modeling or calibrated measurement of the relationship or a combination of both can be determined and used to direct the location of the beam. Alternatively, the functionality of the X-Scan device 195 and the Y-Scan device 197 can be provided by an XY-scan device configured to scan the OCT bean 214 in two dimensions transverse to the Z axis and the propagation direction of the OCT beam 214. The X-scan and Y scan devices 195, 197 change the resulting direction of the OCT beam 214, causing lateral displacements of OCT beam 214 located in the patient's eye 101.

The OCT sample beam 214 is then directed to beam splitter 173 through lens 175 through quarter wave plate 171 and aperture 114 and to the patient eye 101. Reflections and scatter off of structures within the eye provide return beams that retrace back through the patient interface quarter wave plate 171, lens 175, beam splitter 173, y-scan device 197, x-scan device 195, z-scan device 193, optical fiber 196 and beam combiner 204 (FIG. 3), and back into the OCT detection device 220. The returning back reflections of the sample arm 201 are combined with the returning reference portion 206 and directed into the detector portion of the OCT detection device 220, which generates OCT signals in response to the combined returning beams. The generated OCT signals that are in turn interpreted by the controller 60 to determine the spatial disposition of the structures of interest in the patient's eye 101. The generated OCT signals can also be interpreted by the controller to determine the spatial disposition of the structures of interest in the patient's eye 101. The generated OCT signals can also be interpreted by the control electronics to align the position and orientation of the patient eye within the patient interface. As the OCT information can be obtained relatively rapidly (B-scans at 200-500 scans per second) this can be used to provide tracking information to the patient alignment system. That is, the center offset of the corneal vertex can by obtained in x, y and z by determining the highest point in the x and y-slices, and then determining an offset from the desired alignment point. The z value is the difference between the highest corneal point and the desired z location. This information can be fed to an XYZ tracker that aligns the systems either by moving the instrument, the patient's head, or internal mirrors and optical elements in the instrument.

The quarter wave plate 171 described above has the effect that light returning into the instrument will have its polarization rotated by ninety degrees relative to the outgoing polarization. This can result in a situation that the OCT reference beam and signal light incident on the detector 220 will have nearly orthogonal polarizations so that the interference signal generated is extremely weak. One effective method to maximize the signal strength is to set the relevant OCT reference and sample light beams to be linearly polarized with, for example, a polarizing controller in both the sample arm and the reference arm. In one such embodiment, a first set 198 of polarization controllers (FIG. 3A), for example a set of polarization rotating fiber paddle adjusters on the OCT source light output, set the polarization of the incident light on the beamsplitter 173 to be linearly polarized on that surface. Further, a second set 218 of polarization controllers (FIG. 4), such as another set of rotating fiber paddle adjusters, are placed in the reference fiber path leading to the detector 220. Adjustment of the polarization controllers, such as the fiber paddles, will maximize the signal when the reference and signal polarizations match. This allows the system to retain the benefits of having the quarter wave plate 171 for the wavefront sensing portion of the instrument while having minimal impact on the OCT signal strength.

The quarter wave plate 171 may be zero order design at either the OCT wavelength, the wavefront sensor wavelength, or an intermediate wavelength. Practical zero order wave plates made of crossed crystalline quartz plates are low cost and will behave as nearly as ideal over the wavelength range of interests, for instance if the center wavefront sensor wavelength is 840 nm and the center OCT wavelength is 1060 nm. Other alternatives are polymer waveplates or the more expensive achromatic quarter wave plates.

The optical measurement systems according to the present invention preferably comprise an iris imaging subsystem 40. The imaging subsystem 40 generally comprises an infrared light source, preferably infrared light source 152, and detector 141. In operation light from the light source 152 is directed along second optical path 160 to first optical path 170 and is subsequently directed to eye 101 as described above. Light reflected from the iris of eye 101 is reflected back along first optical path 170 to detector 141. In normal use, an operator will adjust a position or alignment of system 100 in XY and Z directions to align the patient according to the image detector array 141. In one embodiment of the iris imaging subsystem, eye 101 is illuminated with infrared light from light source 152. In this way, the wavefront obtained by wavefront sensor 155 will be registered to the image from detector array 141.

The image that the operator sees is the iris of eye 101. The cornea generally magnifies and slightly displaces the image from the physical location of the iris. So the alignment that is done is actually to the entrance pupil of the eye. This is generally the desired condition for wavefront sensing and iris registration.

Iris images obtained by the iris imaging subsystem may be used for registering and/or fusing the multiple data sets obtained by the various subsystems of the present invention, by methods described for instance in "Method for registering multiple data sets," U.S. patent application Ser. No. 12/418,841, which is incorporated herein by reference. As set forth in application Ser. No. 12/418,841, wavefront aberrometry may be fused with corneal topography, optical coherence tomography and wavefront, optical coherence tomography and topography, pachymetry and wavefront, etc. For instance, with image recognition techniques it is possible to find the position and extent of various features in an image. Regarding iris registration images, features that are available include the position, size and shape of the pupil, the position, size and shape of the outer iris boundary (OIB), salient iris features (landmarks) and other features as are determined to be needed. Using these techniques, both patient movement between measurements (and/or during a measurement sequence) can be identified, as well as changes in the eye itself (including those induced by the measurement, such as changes in the size of the pupil, changes in pupil location, etc.).

In many embodiments, an optical measurement system according the present includes a target fixation subsystem 150 (FIG. 1), and an assembly 100 shown in FIGS. 3A and 3B includes fixation target subsystem 180 which includes a fixation target 182 for the patient to view. Fixation target subsystem 180 is used to control the patient's accommodation, because it is often desired to measure the refraction and wavefront aberrations when eye 101 is focused at its far point (e.g., because LASIK treatments are primarily based on this). Cylindrical correction and liquid lenses for the target path may also be used. In the target fixation subsystem, a projection of a target, for instance a cross-hair pattern is projected onto the eye of the patient, the cross hair pattern being formed by a backlit LED and a film. An alternative embodiment is to provide a video target that allows the projection of letters, charts, pictures or movies. One method to control accommodation is to provide the patient with a task "click a button each time you recognize a real word" or "click a button each time the target includes the color purple" in order to insure that the subject is really looking and concentrating on the target.

In operation, light originates from the light source 152 or, alternatively, from video target backlight 182 and lens 186. Lens 185 collects the light and forms an aerial image T2. This aerial image is the one that the patient views. The patient focus is maintained on aerial image 182 during measurement so as to maintain the eye in a fixed focal position.

The operating sequence the optical measurement system and methods of the present is not particularly limited. A scan of the patient's eye may comprise one or more of a wavefront aberrometry measurement of a patient's eye utilising the wavefront aberrometry subsystem, a corneal topography measurement of a patient's eye and an OCT scan of the patient's eye using the OCT substystem, wherein the OCT scan includes a scan at each or one or more locations within the eye of the patient. These locations of the OCT scan may correspond to the location of the cornea, the location of the anterior portion of the lens, the location of the posterior portion of the lens and the location of the retina. In a preferred embodiment, the operating sequence includes each of a wavefront aberrometry measurement, a corneal topography measurement and an OCT scan, wherein the OCT scan is taken at least at the retina, the cornea and one of anterior portion of the patient's lens. Preferably, an iris image is taken simultaneously with or sequentially with an each of measurements taken with wavefront aberrometry subsystem the Corneal Topography Subsystem and the OCT subsystem, including an iris image take simultaneously with or sequentially with the location of each OCT scan. This results in improved accuracy in the 3-dimensional modeling of the patient's eye by permitting the various data sets to be fused and merged into a 3-dimensional model.

Figure 8:
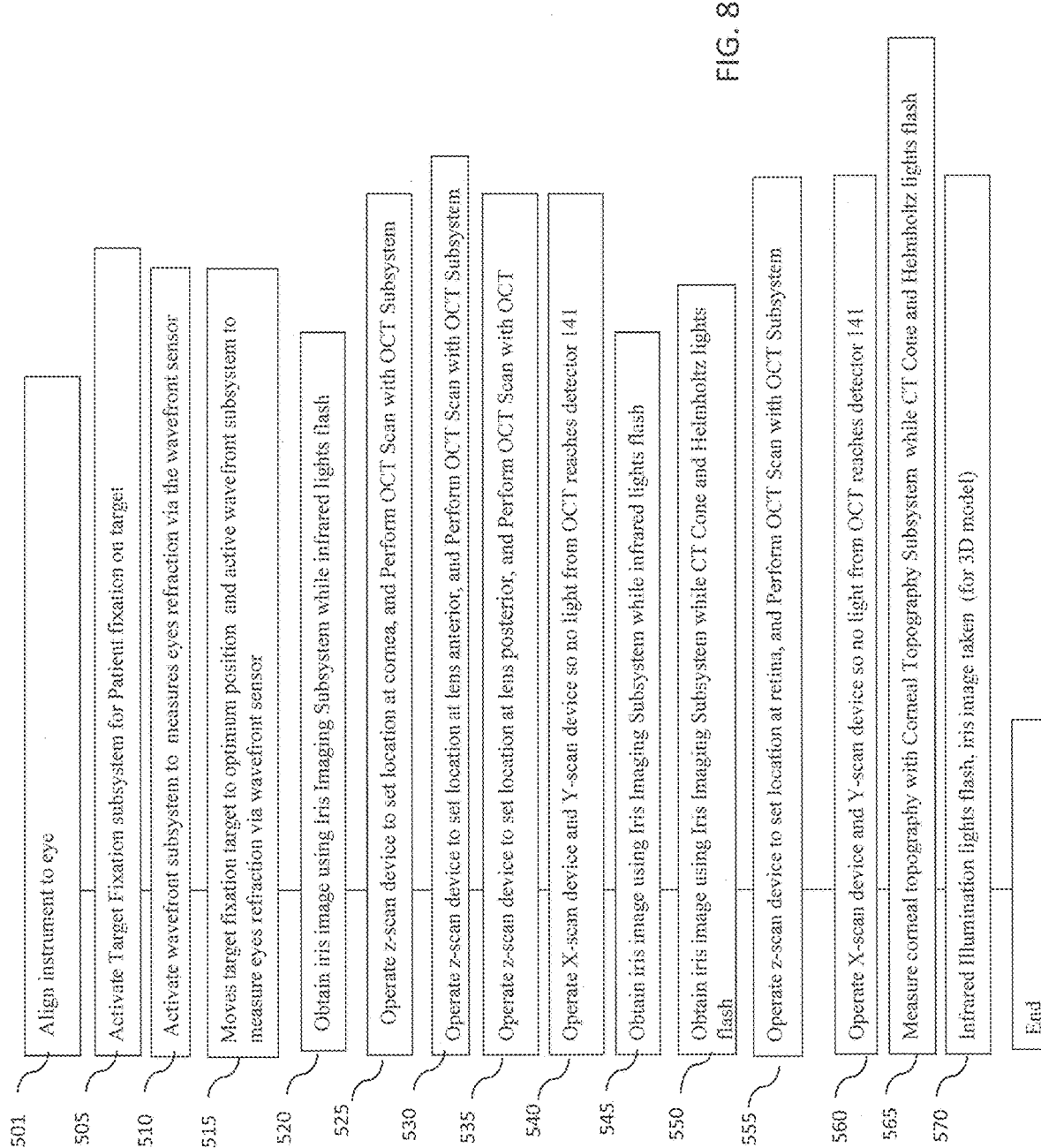
FIG. 8 is a flowchart of an example embodiment of a method for performing cataract diagnostics for an eye with an optical measurement instrument according to one embodiment described herein, including wavefront aberrometry, corneal topography and OCT measurements at various locations with the eye along the axial length of the eye.

FIG. 8 shows one embodiment of an operating sequence and method in which wavefront aberrometry measurements, corneal topography measurements and OCT measurements are all taken. The optical measurement apparatus, including the method of FIG. 8 may be used preoperatively, intra-operatively and/or postoperatively. In the method of FIG. 8, a step 501 comprises aligning the optical measurement system to the eye of the patent. A step 505 comprises activating the Target Fixation subsystem for patient fixation on target. A step 510 comprises activating the wavefront aberrometer subsystem such that the wavefront aberrometer light source 510 is activated and the eye refraction is measured via the wavefront sensor. A step 515 comprises activating the target fixation system to move the target to an optimum position and activate the wavefront aberrometer subsystem such that the wavefront aberrometer light source 152 is activated and the eye refraction is measured via the wavefront sensor 155. A step 520 comprises obtaining an iris image using Iris Imaging Subsystem while infrared light source 152 is operating. A step 525 comprises operating the z-scan device to set OCT scan location at or near cornea, and performing an OCT Scan with the OCT Subsystem. A step 530 comprises operating the z-scan device to set the OCT location at a location at or near the lens anterior and performing an OCT Scan with the OCT Subsystem. A step 535 comprises operating the z-scan device to set the OCT location at a location at or near the lens posterior and performing an OCT Scan with the OCT Subsystem. A step 540 comprises operating the X-scan device and Y-scan device so no light from OCT reaches detector 141. A step 545 comprises obtaining an iris image using the Iris Imaging Subsystem while the infrared light source 152 flashes. A step 550 comprises obtaining an iris image using the Iris Imaging Subsystem while the light sources 120 and helmholz source flash. A step 550 comprises measuring the corneal topography with the Corneal Topography Subsystem. A step 555 comprises operating the z-scan device to set the OCT location at a location at or near the retina and performing an OCT Scan with the OCT Subsystem. A step 560 comprises operating the X-scan device and Y-scan device so no light from OCT reaches detector 141. An optional step 565 comprises measure corneal topography with Corneal Topography Subsystem, which may provide for an improved 3D model of the patient eye. An optional step 570 comprises obtaining an iris image using Iris Imaging Subsystem (for 3D model).

Figure 9:
FIG. 9 is a flowchart of another example embodiment of a method for performing cataract diagnostics for an eye with an optical measurement instrument.

FIG. 9 shows one embodiment of an operating sequence and method in which no wavefront aberrometry measurements are taken. The optical measurement apparatus, including the method of FIG. 8 may be used preoperatively, intra-operatively and/or postoperatively. In the embodiment of FIG. 9, a step 601 comprises aligning the optical measurement system to the eye of the patent. A step 605 comprises activating the Target Fixation subsystem for patient fixation on target. A step 610 comprises obtaining an iris image using Iris Imaging Subsystem while infrared light source 152 is operating. A step 615 comprises operating the z-scan device to set OCT scan location at or near cornea, and performing an OCT Scan with the OCT Subsystem. A step 620 comprises operating the z-scan device to set the OCT location at a location at or near the lens anterior and performing an OCT Scan with the OCT Subsystem. A step 625 comprises operating z-scan device to set the OCT location at a location at or near the lens posterior and performing an OCT Scan with the OCT Subsystem. A step 530 comprises operating the X-scan device and Y-scan device so no light from OCT reaches detector 141. A step 635 comprises obtaining an iris image using the Iris Imaging Subsystem while the infrared light source 152 flashes. A step 640 comprises measuring the corneal topography with the Corneal Topography Subsystem. A step 645 comprises operating the z-scan device to set the OCT location at a location at or near the retina and performing an OCT Scan with the OCT Subsystem. A step 650 comprises operating the X-scan device and Y-scan device so no light from OCT reaches detector 141. An optional step 655 comprises measuring corneal topography with Corneal Topography Subsystem, which may provide for an improved 3D model of the patient eye. An optional step 660 comprises obtaining an iris image using Iris Imaging Subsystem.

Figure 10:
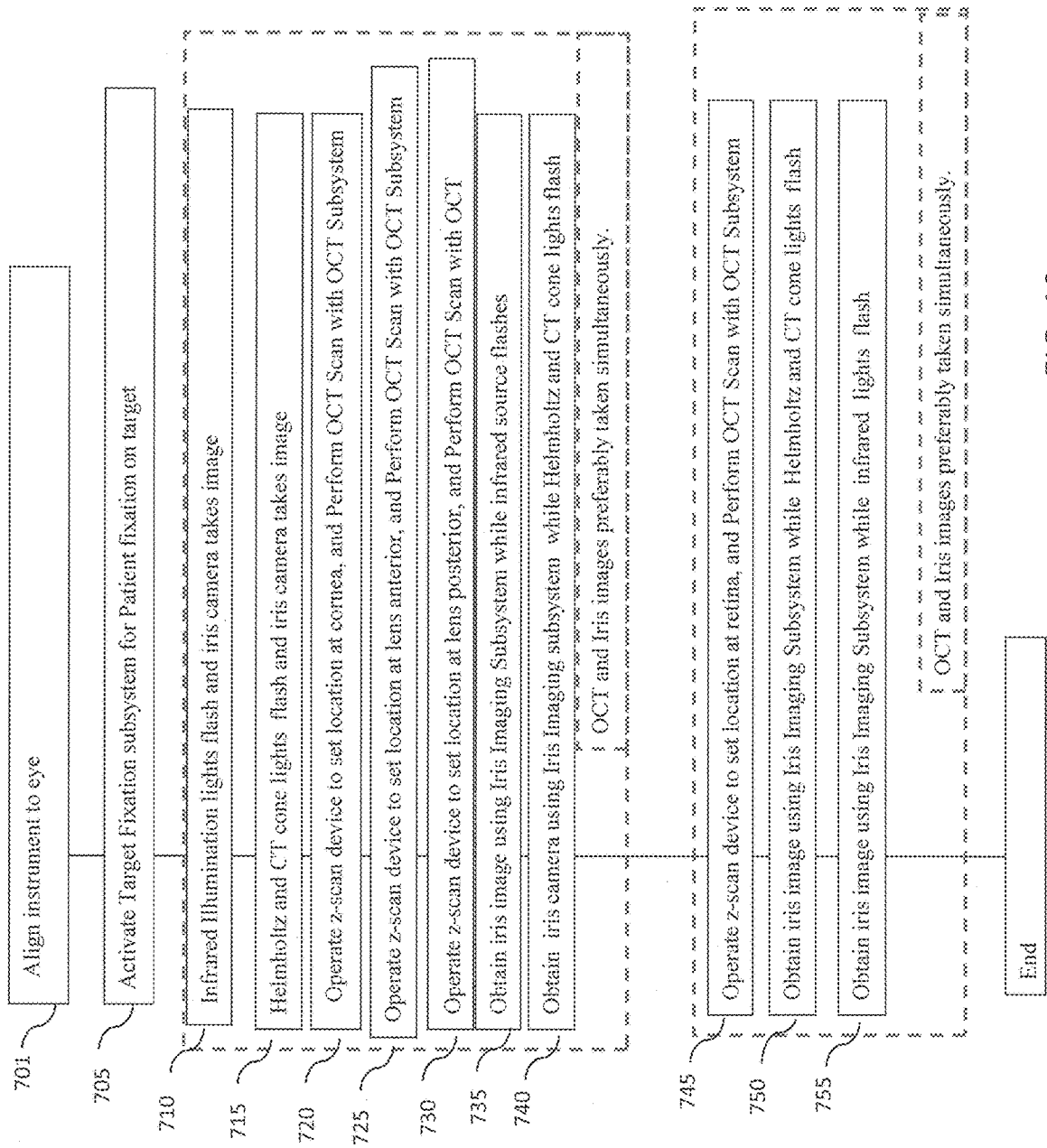
FIG. 10 is a flowchart of another example embodiment of a method for performing cataract diagnostics for an eye with an optical measurement instrument in which OCT measurements and iris imaging may be performed simultaneously.

FIG. 10 shows an embodiment of an operational sequence and method in which OCT measurements utilising the OCT subsystem and Iris images using the iris imaging subsystem may be taken simultaneously in order to improve three dimensional modeling of the patient's eye and improved iris registration of the measurement data sets. The operational sequence of FIG. 10 may be applied to or incorporated into either of the operational sequences and methods of FIG. 8 or 9 as would be readily understood by those ordinarily skilled. In order to effectuate the operating sequence and method of FIG. 10, a lens is inserted into optical path 170 between beam splitter 173 and detector 141. The inserted lens is selected to preferentially pass infrared light used for iris imaging but to block an OCT beam from the OCT light source from reaching detector 141. In this configuration, OCT measurements and iris images may be taken simultaneously. Further, in the embodiment of FIG. 10 a regular speed global shutter iris camera is used operating at 12 frames/second. The operating sequence and method of FIG. 10 may be used preoperatively, intra-operatively and/or postoperatively.

In the embodiment of FIG. 10, a step 701 comprises aligning the optical measurement system to the eye of the patent. A step 705 comprises activating the Target Fixation subsystem for patient fixation on target. A step 710 comprises obtaining an iris image using Iris Imaging Subsystem while infrared light source 152 is operating. A step 715 comprises obtaining an iris image using Iris Imaging Subsystem while corneal topography light sources 120 and Helmholz light source 132 are operating. A step 720 comprises operating the z-scan device to set OCT scan location at or near cornea, and performing an OCT Scan with the OCT Subsystem. A step 725 comprises operating the z-scan device to set the OCT location at a location at or near the lens anterior and performing an OCT Scan with the OCT Subsystem. A step 730 comprises operating z-scan device to set the OCT location at a location at or near the lens posterior and performing an OCT Scan with the OCT Subsystem. A step 735 comprises obtaining an iris image using Iris Imaging Subsystem while infrared light source 152 is operating. A step 740 comprises obtaining an iris image using Iris Imaging Subsystem while corneal topography light sources 120 and Helmholz light source 132 are operating. A step 745 comprises operating the z-scan device to set the OCT location at a location at or near the retina and performing an OCT Scan with the OCT Subsystem. A step 750 comprises obtaining an iris image using Iris Imaging Subsystem while corneal topography light sources 120 and Helmholz light source 132 are operating. A step 755 comprises obtaining an iris image using Iris Imaging Subsystem while infrared light source 152 is operating.

Figure 11:
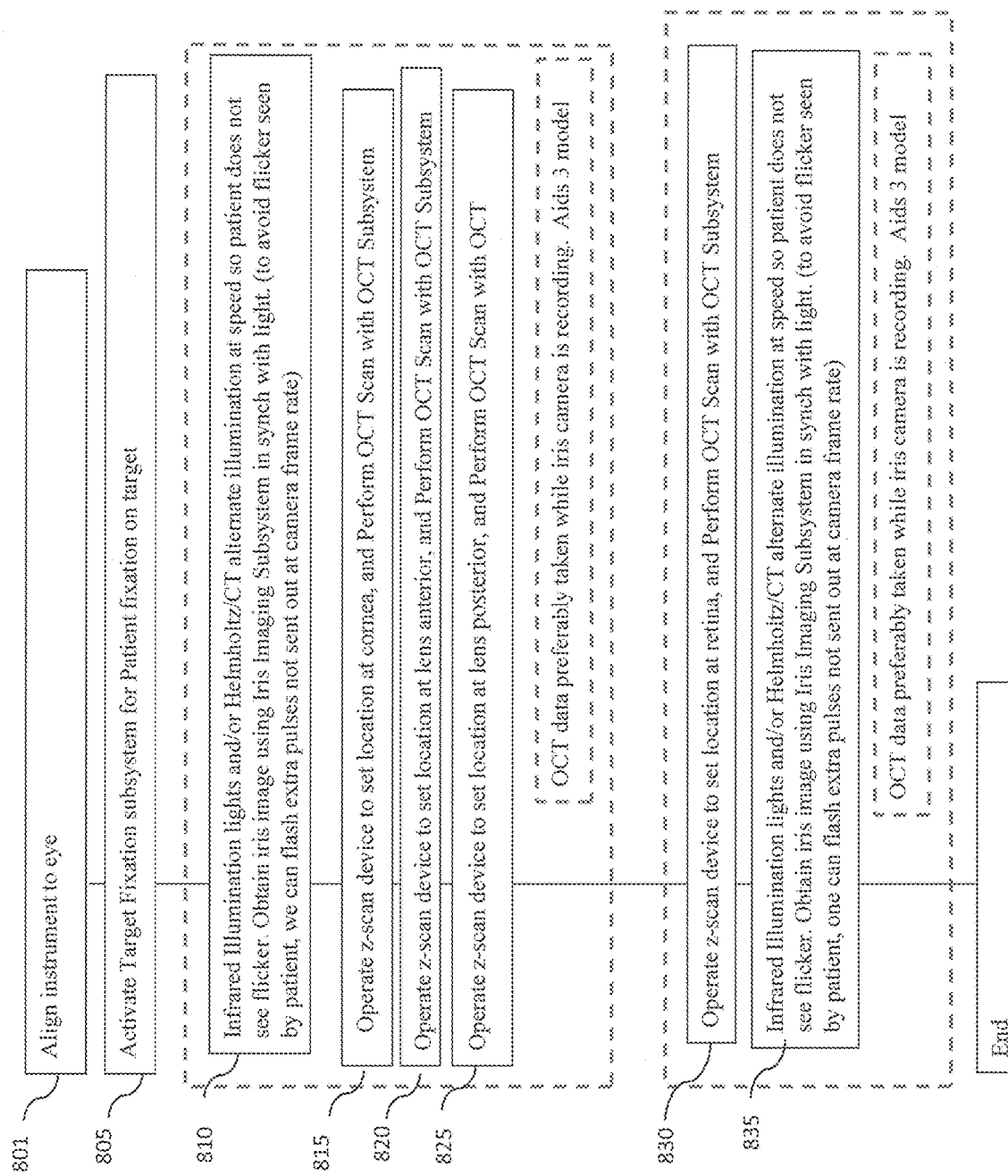
FIG. 11 is a flowchart of yet another example embodiment of a method for performing cataract diagnostics for an eye with an optical measurement instrument in which OCT measurements and iris imaging may be performed simultaneously.

FIG. 11 shows another embodiment of an operational sequence and method in which OCT measurements utilising the OCT subsystem and Iris images using the iris imaging subsystem may be taken simultaneously in order to improve three dimensional modeling of the patient's eye and improved iris registration of the measurement data sets. The operational sequence of this embodiment may be applied to or incorporated into either of the operational sequence and methods of FIG. 8 or 9 as would be readily understood by those ordinarily skilled. As with the method of FIG. 10, in order to effectuate the operating sequence and method of FIG. 11, a lens is inserted into optical path 170 between beam splitter 173 and detector 141. The inserted lens is selected to preferentially pass infrared light used for iris imaging but to block an OCT beam from the OCT light source from reaching detector 141. In this configuration, OCT measurements and iris images may be taken simultaneously. Further, in the embodiment of FIG. 10 a high speed global shutter iris camera, or fast frame rate, is used operating at 60 frames/second. Under the fast frame rate conditions of this embodiment, an infrared illumination source, such as a wavefront aberrometry source, may be used with a one or more second light sources, such as a combination of the corneal topography sources 120 and the Helmholz source, to alternately illuminate a patient's eye repeatedly at short intervals (i.e., alternative short flashes). Under these conditions, the iris imaging subsystem may be synched to the flash from each source so as to capture iris images under both illumination conditions. The operating sequence and method of FIG. 11 may be used preoperatively, intra-operatively and/or postoperatively.

In the embodiment of FIG. 11, a step 801 comprises aligning the optical measurement system to the eye of the patient. A step 805 comprises activating the Target Fixation subsystem for patient fixation on target. A step 810 comprises obtaining an iris image using Iris Imaging Subsystem while infrared light source 152 is operating and obtaining an iris image using Iris Imaging Subsystem while corneal topography light sources 120 and Helmholz light source 132 are operating. This is done by alternately operating the infrared light source and a combination of the corneal topography/Helmholz light sources so as to alternately illuminate the patient's eye with the infrared light source and the combined light sources, preferably at a rate that a patient's eye cannot resolve the "flicker." In this step, the Iris imaging subsystem is in synch with the respective illuminate lights. A step 815 comprises operating the z-scan device to set OCT scan location at or near cornea, and performing an OCT Scan with the OCT Subsystem. A step 820 comprises operating the z-scan device to set the OCT location at a location at or near the lens anterior and performing an OCT Scan with the OCT Subsystem. A step 825 comprises operating z-scan device to set the OCT location at a location at or near the lens posterior and performing an OCT Scan with the OCT Subsystem. A step 830 comprises operating the z-scan device to set the OCT location at a location at or near the retina and performing an OCT Scan with the OCT Subsystem. A step 835 comprises obtaining an iris image using Iris Imaging Subsystem while infrared light source 152 is operating and obtaining an iris image using Iris Imaging Subsystem while corneal topography light sources 120 and Helmholz light source 132 are operating as described above for Step 810.

Placido style-based or spot-based topographers work by shining a pattern of light on the eye. If a patient is looking directly into an instrument, there is often a portion of the cornea that is not illuminated because of a shadow created by the patient's nose. One solution employed by some topographers is to have the patient look into the instrument with about a degree angle. This simply moves the nose relative to the instrument so there is no shadow on the cornea. To aid in orienting the patients head properly, the chin rest often has two ten degree indentations, one for the left eye and the other for the right eye. This solution works well for an instrument that is dedicated to only measuring corneal topography. But it has drawbacks with an instrument that is meant to measure more characteristics of the eye such as refractive state, gaze angle, angle kappa and iris features. In an integrated system that includes a corneal topographer and an OCT system, it is advantageous to combine the results from both into a single display map of corneal topography. In the region where the topographer image is illuminated, the highest accuracy characterization of the optical surface may be obtained. Then in extended regions where the OCT elevation data is available, that information can be used in the same map. The combined map may also include an annular zone that extends beyond the roughly circular region of corneal topographer coverage, Several methods may be used to join the OCT data set to the placido style spot based topographer data set. One method is to use as a reference an image taken with the same camera as the topographer but with the topographer pattern turned off and simple illumination from one or a few light sources turned on. Another is to have the scan mirrors from the OCT pause momentarily at certain locations so light from the OCT is bright enough to be seen on the camera. Another is to perform XY polynomial shape fits on both OCT and topographer data sets and join those together in best fit method. In that case the OCT data that is collected in the same region as the topographer data is being used to assist in performing the match. Another more direct method is simply to have done a step at a previous point in time, for instance during manufacture and calibration, where the relationship between the OCT scan pattern and image locations on the camera have been established. This may be done simply by placing a reflective target at the measurement plane and recording images of the scan pattern of the OCT. In theory, in an ideal system the entirety of the OCT beam would be going into the OCT measurement optical path, but in practice it is found that a very small amount of light leakage at the OCT wavelength that reaches the camera is sufficient to perform such a calibration.

Figure 12:
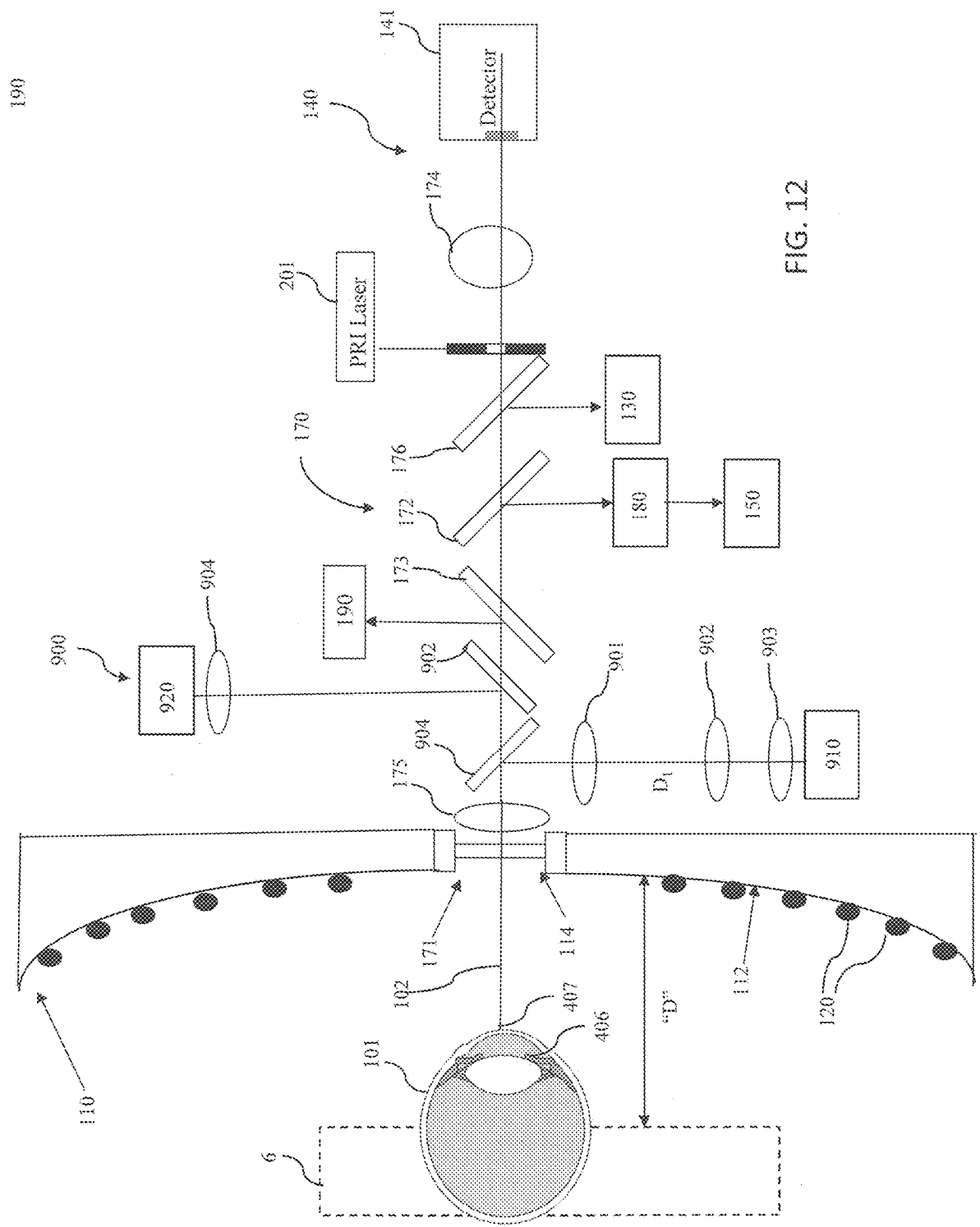
FIG. 12 illustrates another embodiment of a suitable configuration and integration of an optical coherence tomographer subsystem, a wavefront aberrometer subsystem, a corneal topographer subsystem, an iris imaging subsystem, a fixation target subsystem and a posterior corneal astigmatism subsystem according to a non-limiting embodiment of the present invention.

FIG. 12 is a simplified block diagram illustrating an assembly 100 according to another embodiment of the present invention that further comprises a posterior corneal astigmatism assembly 900. Except for the inclusion of the posterior corneal astigmatism assembly, the other components may be same as are described with respect to FIGS. 1-11. Specifically, the assembly 100 according to many embodiments includes an the optical coherence tomographer (OCT) subsystem 190, the wavefront aberrometer subsystem 150, the corneal topographer subsystem 140 for measuring one or more characteristics of a subject's eye, an iris imaging subsystem 40, the fixation target subsystem 180 and the shared optics 50 as described above with respect to FIGS. 1-11.

The posterior corneal astigmatism assembly 900 generally comprises a first detector 910 at a first effective optical distance $D_1$ from a predetermined location anterior or posterior to the patient's cornea and a second detector 920 at a second effective optical distance $D_2$ from the predetermined location. In many embodiments, the effective optical distance $D_1$ is less than the effective optical distance $D_2$. In these embodiments, the first detector 910 is referred to as the near detector and the second detector 920 is referred to as the far detector. The first and second detectors 910, 920 are generally detectors suitable for detecting visible and/or infrared light, such as a CCD, and more specifically capable of detecting light reflected from the patient's eye.

Figure 13A:
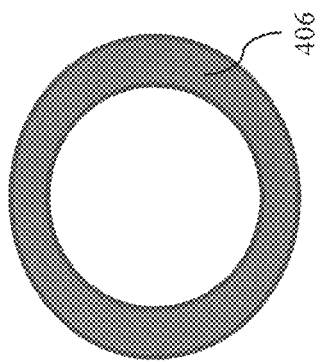
FIG. 13A illustrates an image obtained from a near detector of a posterior corneal astigmatism subsystem according to a non-limiting embodiment of the present invention.
Figure 13B:
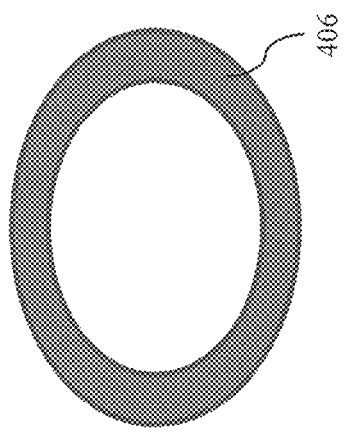
FIG. 13B illustrates an image obtained from a far detector of an a posterior corneal astigmatism assembly according to a non-limiting embodiment of the present invention.

Without being limited to theory, the posterior corneal astigmatism assembly 900 is based on the principle that the amount of distortion of an object by a toric lens that is detected by a detector depends on a distance of the detector from the toric lens. More specifically, the amount of detected distortion increases with increasing distance from the toric lens. For example, when a toric spectacle lens is placed in front of a patient's eye, it introduces distortion into the image the patient perceives. Because of the action of the toric lens in these instances, a patient may perceive a physically round object as a distorted oval with the axis of the oval pointing along the axis of the astigmatism. Further, the closer the lens is to the eye, the less distortion the patient perceives. For instance, a toric contact lens on a patient's eye may cause almost no perceivable distortion. FIG. 13A illustrates an image detected of a round object by a detector with a toric lens disposed between the round object and the detector when the detector is near the toric lens. FIG. 13B illustrates an image detected of a round object by a detector with a toric lens disposed between the round object and the detector when the detector is further from the toric lens.

The same principle can be applied to the situation where the cornea itself replaces the toric lens in the preceding example. In brief, the total astigmatism and the posterior corneal astigmatism of the patient's eye are obtained by measuring the effect of the cornea on light reflected from one or more structures posterior to the cornea within the patient's eye. In accordance with many embodiments, two detectors 910, 920 located at different effective optical distances $D_1$, $D_2$ from the eye, obtain simultaneous images of a predetermined structural feature posterior to the cornea within the patient's eye. Optical elements 904, 902, preferably beam splitters, deflect light from the optical axis 102 to the near detector 910 and the far detector 920, respectively. Light reflected from within the eye provides structural information regarding a predetermined structure in the patient's eye, passes through the cornea and is detected by both the near detector 910 and the far detector 920. The near detector 910 at the shorter effective optical distance $D_1$ from the predetermined structure represents the less distorted image of the predetermined structure. In many embodiments, the near detector may be sufficiently close to the patient's eye that it may be deemed an undistorted image of the predetermined structure. The far detector 920 at the longer effective optical distance $D_2$ is characterized has having a greater distorted image of the target structure. In connection with the posterior corneal astigmatism assembly of many embodiments, the amount of distortion at the far detector 920, preferably in comparison to the image from the first detector 910, reveals the total corneal astigmatism of the eye.

The predetermined structure imaged by the near detector 910 and the far detector 920 is preferably the iris 406, and more preferably, a boundary of the iris. In principle, the strongest distortion effect would be expected when the predetermined structure being imaged is at the focus point of the cornea. However, the focus point of the cornea (410, FIG. 5) is the retina (476, FIG. 5), and the crystalline lens (402, FIG. 5) of the eye is between the cornea and the lens. The presence of the lens significantly complicates any attempt to look at retinal features for corneal distortion analysis. Conversely, the iris of the eye lies in between the cornea and the lens, which eliminates the lens as a confounding factor. As a result, in a preferred embodiment, the predetermined structure to be imaged is the iris, or more specifically, a boundary thereof. To obtain a clear iris boundary, an infrared light source is directed onto the retina. In a preferred embodiment, back scatter from the retina uniformly back illuminates the pupil of the eye, passes the cornea and is detected substantially simultaneously by the near detector 910 and the far detector 920 to produce iris images at the first effective optical distance $D_1$ and the second effective optical distance $D_2$.

In some embodiments, an effective optical distance is a physical distance between a predetermined location anterior to the iris, or anterior to the cornea, and a detector, preferably an entrance pupil of the detector. The predetermined location is preferably in a location at or near the apex 407 of the cornea. In some embodiments, the predetermined location is less than 2 mm from the apex 407 of the cornea or less than 1 mm from the apex of the cornea. Conversely, one or more optical elements 901, 902 may be used to optically relay the entrance point of the detector to a second predetermined location, for instance to a predetermined location at or near the apex of the cornea. When optical elements 901, 902 are used to relay a position of a detector, the effective optical distance is a distance between the predetermined location and the relayed position of the detector. The optical relay the detector's entrance pupil of may be relayed by a telescope, such as a 4F telescope, or holographic optical elements.

When clinically feasible, the near detector 910 may be physically placed at or very near to the apex of the cornea of the eye. However, in practice, this will typically be inconvenient clinically. Instead, it is advantageous to optically relay the entrance pupil of the near detector 910 to near the apex of the cornea by means of a telescope, such as a 4F telescope. Holographic optical elements can serve the same purpose.

In some embodiments, the relay of the near detector 910 by, for instance, the 4F telescope, also makes it possible to position the entrance pupil of the near detector 910 to be a few millimeters within the eye, at the eye's exit pupil instead of the corneal apex. This plane is the virtual image of the iris of the eye as seen underneath the cornea. In human eyes, this location varies over a narrow range of less than 2 mm. In either case, whether the entrance pupil is relayed to the corneal apex or iris, the near detector 910, such as a camera, is focused on the iris feature to obtain the image for the data analysis. A lens 903 may be used to direct the back reflected to the near detector 910.

The far detector 920 may generally be placed at any suitable effective optical distance. In many embodiments, a suitable effective optical distance for the far detector 920 is between about 50 mm and 500 mm, or between about 100 mm and 300 mm or about 100 mm to 200 mm. Like the near detector 910, the far detector 920, such as a camera, is preferably focused on the iris when the image is obtained for the data analysis. In some embodiments, a camera lens 904 with a long zoom may be placed remotely from the eye to direct to the light to the far detector 920.

In some embodiments, images from the near detector 910 and far detector 920 are obtained at two or more eye pupil diameters. This can be achieved by changing a target light brightness to control pupil diameter. The near and far detectors can be configured to acquire image simultaneously at the different pupil diameters to obtain the best data set for analysis.

The simultaneous imaging by near detector 910 and far detector 920 provides the total corneal astigmatism. To find the posterior corneal astigmatism, the anterior corneal astigmatism is subtracted from the total corneal astigmatism. This can be done, for instance, with vectoral methods to get the axis correct as is known to those ordinarily skilled. The amount of distortion seen by the far detector 920 is proportional to the distance that the iris is from the apex of the cornea. As such, the accuracy of the total corneal astigmatism and posterior corneal astigmatism calculations can be improved if an accurately measured anterior chamber depth is included.

Preferably, the anterior corneal topographer needed to obtain the anterior corneal astigmatism is incorporated into the optical measurement system 1 described herein that includes a corneal topographer subsystem shown in FIGS. 2, 3A and 3B. However, the anterior corneal topography may be performed on a separate instrument and can be based for instance on a placido style-based or spot-based corneal topographer.

Figure 14:
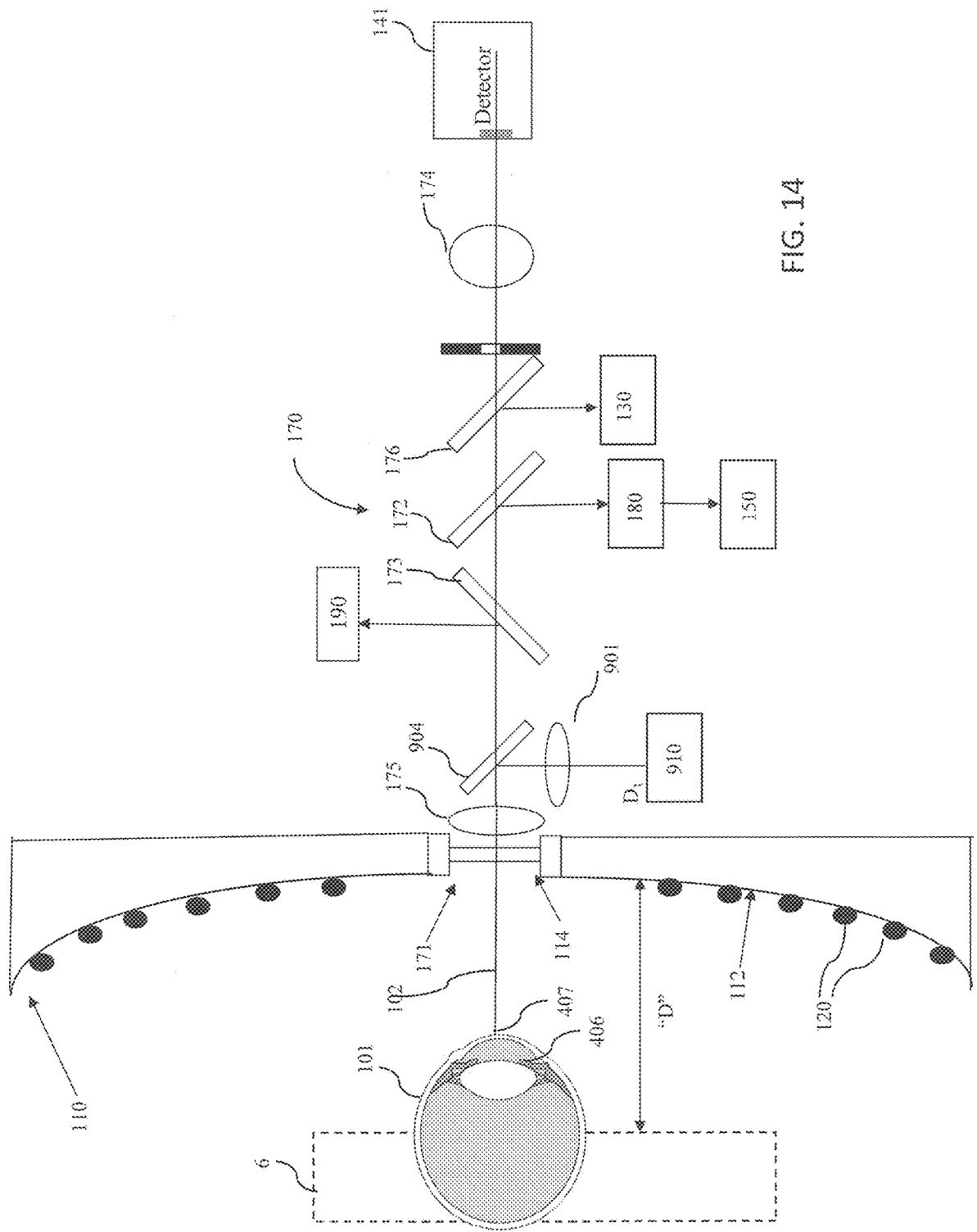
FIG. 14 illustrates an alternate having near and far detectors that can be used to determine a total corneal astigmatism.

FIG. 14 shows an alternate arrangement exhibiting the near and far detectors that can be used to determine the total corneal astigmatism. The near detector 910 is located an effective distance of D1 from the eye. The pair of lenses 901 and 175 together behave as a single effective lens so that the effective lens focal length may be calculated according to the well-known "lens maker equation" and the distance from the lens 175 to the eye is greater than that effective lens focal length. The distance of the detector 910 from lens 901 is set so that the detector is focused on the iris of the eye. In FIG. 14, the detector 141 is the far detector. The lenses 175 and 174 are separated by the sum of their focal lengths making them an afocal system. Effectively, the light patterns received by the camera from the eye is the same as that obtained from a detector located far away.

Figure 15:
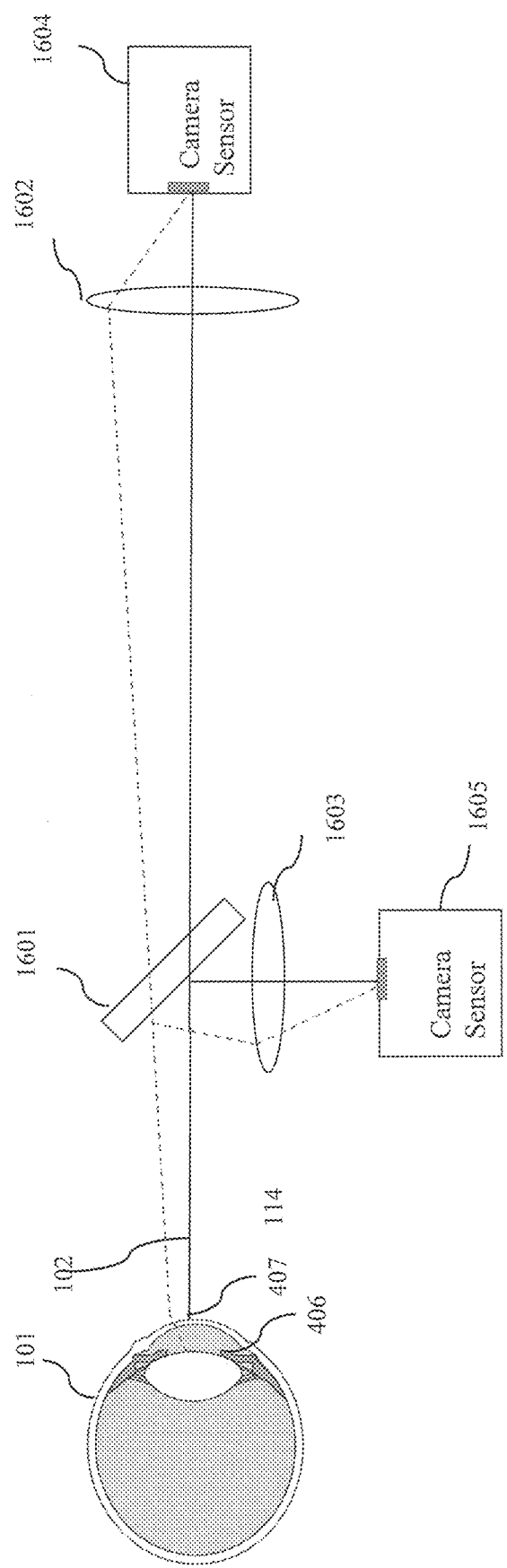
FIG. 15 shows the far and near detectors operating as a separate system to determine a total corneal astigmatism.

FIG. 15 shows the far and near detectors operating as a separate system for determining the total corneal astigmatism of a patient's eye. Two cameras view the eye. The dashed lines show rays that indicate the imaging condition. The eye iris 406 eye is imaged through the cornea 407. In the presence of astigmatism on the cornea, the imaging condition may not be exactly satisfied but the offset from the ideal best focus is small enough that a clear image of the iris still appears on the camera sensors 1604 and 1605. In practice the spherical power of the cornea is about 43 diopters and the cylindrical optical power of the cornea is typically about one to two diopters. The beam splitting element 1601 sends light into both optical paths. The lens 1603 has a shorter focal length than the lens 1602. So the camera sensor 1605 is considered the near detector and camera sensor 1604 is the far detector. For the purpose of illustration, we can consider the case when the iris 406 of the eye has a circular shape. Then if the cornea 407 has a low strength of astigmatism, the image seen on both near and far cameras is circular. But when the cornea has strong astigmatism, the near camera sees a substantially circular iris as in FIG. 13A while the far camera sees an elliptical pattern as in FIG. 13B. The orientation of the ellipse also shows the angle of the astigmatic axis. However, in most eyes, the iris 406 inside the eye has a slightly elliptical shape, so it is not possible to deduce the astigmatism of the eye solely from far camera image alone. The comparison of the ellipticity between the image gives the total corneal astigmatism. Determination of the strength of the cylinder may be accomplished by analyzing the short and long axes of the ellipse and applying the thin lens imaging equation to long and short axes independently.

Figure 16:
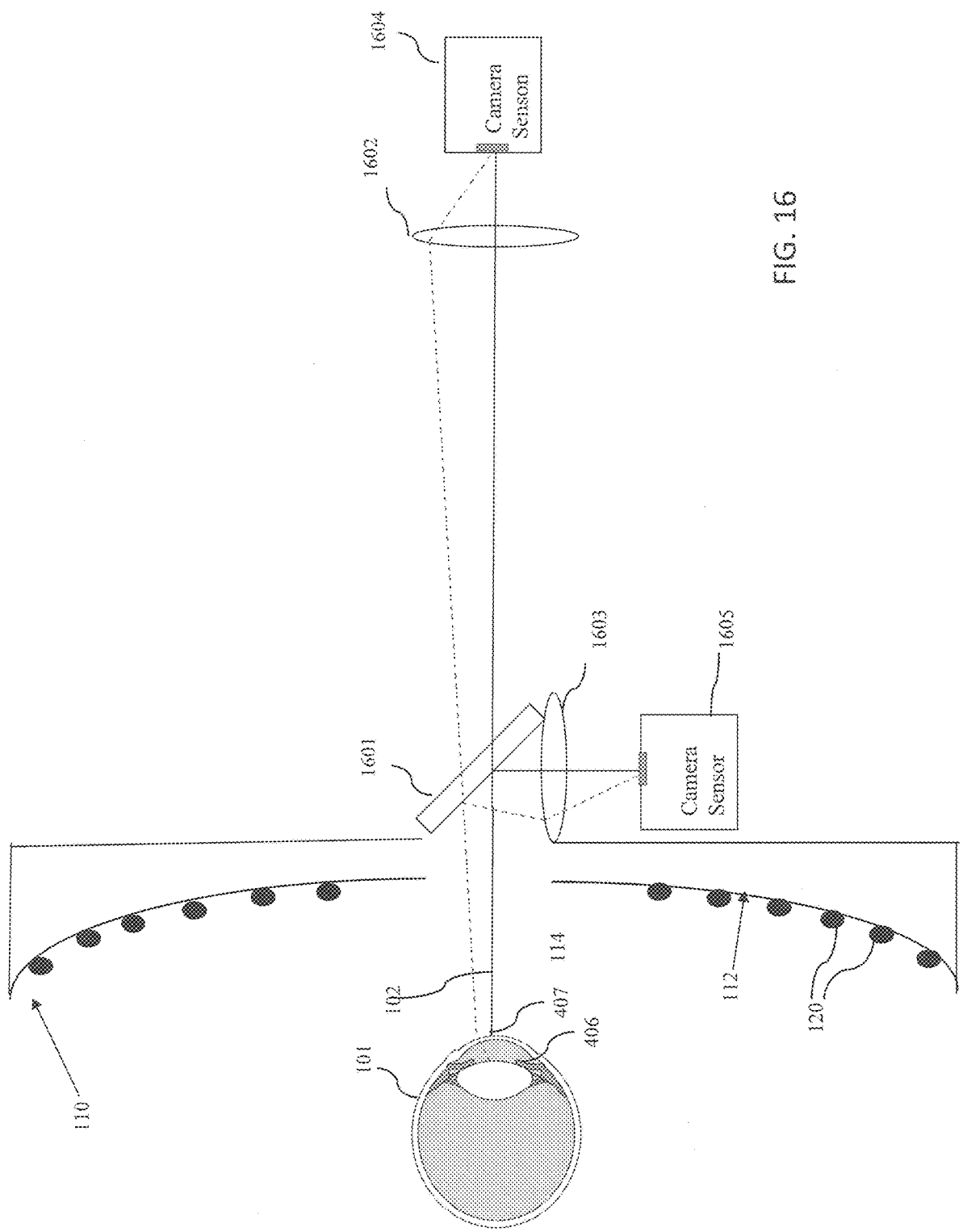
FIG. 16 shows an embodiment of FIG. 15 in which a corneal topographer has been added.

FIG. 16 shows the addition of the corneal topographer to the total corneal astigmatism system depicted in FIG. 15. The topography data may be analyzed to give the anterior spherical power and astigmatism of the anterior of the cornea. Simple subtraction of the anterior cylinder power from the total corneal astigmatism gives the posterior astigmatism power.

The arrangement of the near detector 910 and far detector 920 also makes it possible to calculate range to an object by comparing object sizes by known triangulation techniques or by other ray tracing means known to those ordinarily skilled.

The posterior corneal astigmatism assembly 900 may be used in LASIK surgery to improve results by accurately measuring posterior corneal astigmatism.

The optical measurement instrument 1 and the optical measurements obtained therewith may be used pre-operatively, i.e. before a cataract surgery or other surgical procedure, for, e.g., eye biometry and other measurements, diagnostics and surgical planning. Surgical planning may include one or more predictive models. In the one or more predictive models, one or more characteristics of the postoperative condition of the patient's eye or vision is modeled based on one or more selected from the group consisting of pre-operative measurements obtained from the optical measurement instrument 1, a contemplated surgical intervention, and on or more algorithms or models stored in the memory of the optical measurement system 1 and executed by the processor. The contemplated surgical intervention may include the selection of an IOL for placement, the selection of an IOL characteristic, the nature or type of incision to be used during surgery (e.g., relaxation incision), or one or more post-operative vision characteristics requested by the patient.

The optical measurement instrument 1 and the optical measurements obtained therewith may be used intra-operatively, i.e., during a cataract surgery or other surgical procedure, for, e.g., intraoperative eye diagnostics, determining IOL position and/or orientation, surgical planning, and control/or of a laser surgical system. For instance, in the case of laser cataract surgical procedure, any measurement data obtained preoperatively by the optical measurement instrument may be transferred to a memory associated with a cataract laser surgical system for use before, during or after either the placement of a capsulotomy, fragmentation or a patient's lens or IOL position and/or orientation during the cataract surgery. In some embodiments, measurements using optical measurement instrument 1 may be taken during the surgical procedure to determine whether the IOL is properly placed in the patient's eye. In this regard, conditions measured during the surgical procedure may be compared to a predicted condition of the patient's eye based on pre-operative measurements, and a difference between the predicted condition and the actual measured condition may be used to undertake additional or corrective actions during the cataract surgery or other surgical procedure. The corrective procedure may also be merely based on intraoperative measurements so that the actual measured condition dictates the action that is needed to provide the desired outcome.

The optical measurement instrument 1 and the optical measurements obtained therewith may be used postoperatively, i.e., after a cataract surgery or other surgical procedure, for, e.g., post-operative measurement, postoperative eye diagnostics, postoperative IOL position and/or orientation determinations, and corrective treatment planning if necessary. The postoperative testing may occur sufficiently after the surgery that the patient's eye has had sufficient time to heal and the patient's vision has achieved a stable, postsurgical state. A postoperative condition may be compared to one or more predicted condition performed pre-operatively, and a difference between the preoperatively predicted condition and the postoperatively measured condition may be used to plan additional or corrective actions during the cataract surgery or other surgical procedure. The corrective procedure may also be merely based on intraoperative measurements so that the actual measured condition dictates the action that is needed to provide the desired outcome.

Instrument 1 stores all the biometric data and postoperative information in an embedded database, so that the data contained in this database can be used to further optimize or generate new algorithms to improve future patient's outcomes. In certain embodiments, these algorithms are related to optimize actual lens position prediction, surgically induced astigmatism, IOL constants or personalized regressions to account for corneal spherical aberration in IOL power calculations for post-LASIK eyes.

The optical measurement instrument 1, including the Corneal Topography Subsystem, the OCT subsystem and the wavefront aberrometry subsystem, utilising a suitable operating sequence as disclosed herein, is operable to measure one, more than one or all of the following: ocular biometry information, anterior corneal surface information, posterior corneal surface information, anterior lens surface information, posterior lens surface information, lens thickness information, lens tilt information and lens position information. In some embodiments, the ocular biometry information may include a plurality of central corneal thicknesses (CCT), an anterior chamber depth (ACT), a pupil diameter (PD), a white to white distance (WTW), a lens thickness (LT), an axial length (AL) and a retinal layer thickness. This measurement data may be stored in memory 62 associated with controller 60. The plurality of characteristics may be measured preoperatively, and where appropriate, intra-operatively, and postoperatively.

In some embodiments, memory 62 associated with controller 60 may store intraocular lens (IOL) model data for a plurality of IOL models, each of the IOL models having associated with it a plurality of predetermined parameters selected from the group consisting of dioptic power, refractive index and dispersion, asphericity, toricity, echellete features, haptic angulation, and lens filter. The IOL data may be used by one or more processors of optical measurement instrument 1, in conjunction with measurement data of a subject's eye obtained by optical measurement instrument 1, for cataract diagnostics or cataract treatment planning, which may include specifying and/or selecting a particular IOL for a subject's eye. For example, one or more processors of optical measurement instrument 1 may execute an algorithm which includes: accessing the plurality of IOL models stored in, and for each of the IOL models: (1) modeling the subject's eye with an intraocular lens corresponding to the IOL model and the measured characteristics of the subject's eye; (2) simulating the subject's eye based on the plurality of IOL predetermined parameters and the predicted IOL position; (3) performing one of a ray tracing and a power calculation based on said model of the subject's eye; and (4) selecting an IOL for the subject's eye from the plurality of IOL models corresponding to the optimized IOL based on a predetermined criteria.

In some embodiments, one or more processors of optical measurement instrument 1 may execute an algorithm comprising: determining a desired postoperative condition of the subject's eye; empirically calculating a post-operative condition of the eye based at least partially on the measured eye characteristics; and predictively estimating, in accordance with an output of said empirically calculating and the eye characteristics, at least one parameter of an intraocular lens for implantation into the subject's eye to obtain the desired postoperative condition.

In many embodiments, the eye imaging and measurement system further comprises a memory operable to store Intraocular Lens ("IOL") Data, the IOL data including a plurality of dioptic power, anterior and posterior radius, IOL thickness, refractive index and dispersion, asphericity, toricity, echelette features, haptic angulation, and lens filter.

In many embodiments, the eye imaging and measurement system further comprises a memory operable to store intraocular lens ("IOL") model data for a plurality of IOL models, IOL model having associated with a plurality of predetermined parameters selected from the group consisting of dioptic power, anterior and posterior radius, IOL thickness, refractive index and dispersion, asphericity, toricity, echelette features, haptic angulation, and lens filter.

An improved system for selecting an intraocular lens (IOL) for implantation, comprises: a memory operable to store data acquired from each of the Corneal Topography Subsystem, the wavefront sensor subsystem and the Optical Coherence Tomography subsystem, wherein the stored data includes a plurality of ocular biometry information, anterior corneal surface information, posterior corneal surface information, anterior lens surface information, and posterior lens surface information, lens tilt information, lens thickness information, and lens position information; the memory further operable to store intraocular lens ("IOL") model data for a plurality of IOL models, IOL model having associated with it a plurality of predetermined parameters selected from the group consisting of dioptic power, anterior and posterior radius, IOL thickness, refractive index and dispersion, asphericity, toricity, echelette features, haptic angulation, and lens filter; and a processor coupled to the memory, the processor deriving the treatment of the eye of the patient applying, for each of the plurality of identified IOL Model, to: (1) predict a position of one of the identified IOL Models when implanted in the subject eye, based on the plurality of characteristics; (2) simulate the subject eye based on the plurality of IOL predetermined parameters and the predicted IOL position; (3) perform one or more of ray tracing and an IOL spherical equivalent (SE) and cylinder (C) power calculation, as well as optionally, to determine the optimum IOL orientation based on said eye model; and (4) propose one IOL power for one or more IOL models from the plurality of IOLs corresponding to the optimized IOL(s) based on predetermined criteria; and (5) show the simulated optical quality and/or visual performance provided by each of the proposed IOL models for distance and/or for any other vergence and/or field angle.

A method of selecting an intraocular lens (IOL) to be implanted in a subject's eye, comprising: measuring a plurality of eye characteristics comprising ocular biometry information, anterior corneal surface information, posterior corneal surface information, anterior lens surface information, and posterior lens surface information, lens tilt information, lens thickness information and lens position information; and for each of Intraocular Lens ("IOL") model having associated with it a plurality of predetermined parameters selected from the group consisting of dioptic power, refractive index and dispersion, anterior and posterior radius, IOL thickness, asphericity, toricity, echelette design, haptic angulation, and lens filter: (1) modeling the subject eye with the intraocular lens; (2) simulating the subject eye based on the plurality of IOL predetermined parameters and the predicted IOL position; (3) performing a ray tracing and an IOL spherical equivalent (SE) and cylinder (C) power calculation, as well as determine the optimum IOL orientation based on said eye model; and (4) proposing one IOL power for one or more IOL models from the plurality of IOLs corresponding to the optimized IOL(s) based on predetermined criteria; and optionally (5) show the simulated optical quality and/or visual performance provided by each of the proposed IOL models for distance and/or for any other vergence and/or field angle.

A tangible computer-readable storage device storing computer instructions which, when read by a computer, cause the computer to perform a method comprising: receiving a plurality of eye characteristics comprising ocular biometry information, anterior corneal surface information, posterior corneal surface information, anterior lens surface information, and posterior lens surface information, lens tilt information, lens thickness information and lens position information; for each of Intraocular Lens ("IOL") model having associated with it a plurality of predetermined parameters selected from the group consisting of dioptic power, refractive index and dispersion, anterior and posterior radius, IOL thickness, asphericity, toricity, echelette design, haptic angulation, and lens filter: (1) simulating a geometry of the subject eye with each of the plurality of intraocular lenses (IOL) implanted, in accordance with the plurality of eye characteristics; (2) performing a ray tracing and an IOL spherical equivalent (SE) and cylinder (C) power calculation, as well as optionally determining the optimum IOL orientation based on said eye model; (3) proposing one IOL power for one or more IOL models from the plurality of IOLs corresponding to the optimized IOL(s) based on predetermined criteria; and optionally (4) showing the simulated optical quality and/or visual performance provided by each of the proposed IOL models for distance and/or for any other vergence and/or field angle.

A method of predicting the intraocular lens position comprising: determining a plurality of eye characteristics before cataract surgery, comprising ocular biometry information, anterior corneal surface information, posterior corneal surface information, anterior lens surface information, and posterior lens surface information, lens tilt information, lens thickness information and lens position information; determining a plurality of eye characteristics after cataract surgery, comprising ocular biometry information, anterior corneal surface information, posterior corneal surface information, anterior IOL surface information, and posterior IOL surface information, IOL tilt information, and IOL position information; calculating or measuring, based on a mathematical relationship, a distance from the apex or from the retina to a plane of the intraocular lens after an ocular surgical procedure; calculating an optical power of the intraocular lens suitable for providing a predetermined refractive outcome; wherein a mathematical relationship is found between the preoperative and postoperative eye characteristics that accurately predict the measured distance from the apex or from the retina to the plane where the intraocular lens is. In a certain embodiment, the method herein described to predict the IOL position may depend on the IOL model and/or patient's biometric configurations.

An improved system for planning a refractive treatment of an eye of a patient, the system comprising: a memory operable to store eye measurement data comprising ocular biometry information, anterior corneal surface information, posterior corneal surface information, anterior lens surface information, and posterior lens surface information, lens tilt information and lens position information; a processor coupled to the memory, the processor deriving the treatment of the eye of the patient applying an effective treatment transfer function, wherein the effective treatment transfer function is derived from, for each of a plurality of prior eye treatments, a correlation between a pre-treatment vector characterizing the eye measurement data before treatment, and a post-treatment vector characterizing post-treatment eye measurement data of the associated eye; an output coupled to the processor so as to transmit the treatment to facilitate improving refraction and/or higher order aberration and/or optical quality of the eye of the patient for one or more multiple vergences and/or field angles. The processor preferably comprises tangible media embodying machine readable instructions for implementing the derivation of the treatment.

An improved method for planning a refractive treatment of an eye of a patient, the system comprises: measuring a plurality of ocular biometry information, anterior corneal surface information, posterior corneal surface information, anterior lens surface information, and posterior lens surface information, lens tilt information, lens thickness information and lens position information.

A method of customizing at least one parameter of an intraocular lens, comprising: measuring a plurality of eye characteristics comprising ocular biometry information, anterior corneal surface information, posterior corneal surface information, anterior lens surface information, and posterior lens surface information, lens tilt information and lens position information; determining a desired postoperative condition of the eye; empirically calculating a post-operative condition of the eye based at least partially on the measured eye characteristics; and predictively estimating, in accordance with an output of said empirically calculating and the eye characteristics, the at least one parameter of the intraocular lens to obtain the desired postoperative condition.

A method of adjusting the refractive refraction in an eye of a patient who has undergone cataract surgery comprising: measuring a plurality of post-operative eye characteristics in an eye of a patient who has previously undergone cataract surgery, the eye characteristics comprising ocular biometry information, anterior corneal surface information, posterior corneal surface information, anterior lens surface information, and posterior lens surface information, lens tilt information and lens position information; identifying a plurality of corrective procedure based at least partially on one of (1) a comparison of at least one measured pre-operative eye characteristic and the corresponding measured post-operative eye characteristic; and (2) a comparison of at least one predicted post-operative eye characteristic and the corresponding measured post-operative eye characteristic; for each of a plurality of corrective procedures: modeling the subject eye with the corrective procedure; modeling the subject eye based on the corrective procedure; performing one of a ray tracing and a power calculation based on said eye model; and selecting a corrective procedure from the plurality of IOL models and/or orientations corresponding to the optimized IOL model and/or orientation based on a predetermined criteria. In certain embodiments, the adjustment is merely based on postoperative measurements so that the actual measured condition dictates the action that is needed to improve the refraction of the patient.

In some embodiments, the system further comprises a processor configured to execute an algorithm. The algorithm comprises, for each of the IOL models: (1) modeling the subject's eye with an intraocular lens corresponding to the IOL model and the measured characteristics of the subject's eye; (2) simulating the subject's eye based on the plurality of IOL predetermined parameters and the predicted IOL position; (3) performing one of a ray tracing and a power calculation based on said model of the subject's eye; and (4) selecting an IOL from the plurality of IOL models corresponding to the optimized IOL based on a predetermined criteria.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by the structure particularly pointed out in the written description, claims and the appended drawings.

In another embodiment, the systems and methods of the present include methods of determining an intraocular lens as described in U.S. Pat. No. 8,696,120, entitled "System and Methods for Determining Intraocular Lens Power," the entire contents of which are incorporated herein by reference. As described in U.S. Pat. No. 8,696,120, a number of ocular parameters are used in deriving an appropriate lens power for implantation into the eye. These parameters include axial length (AL), corneal radius (CR) or power (K), and anterior chamber depth prior to surgery (ACDpre), among others. In general, one or more of these parameters are used to provide the preoperative estimation of the postoperative effective lens position (ELP), which is related to the IOL's principal plane, although it may be modified depending on the surgeon through the optimization of the corresponding IOL constant. The ELP is then used in combination with one or more of these same parameters to provide an estimate of the correct lens power to provide a desired refractive outcome (typically emmetropia). As shown in U.S. Pat. No. 8,696,120, the combined measurements of VLpre, ACDpre, and LT are highly predictive in calculating the postoperative vitreous length, from which the position of an implanted intraocular lens or optic can be derived if its thickness is known. The calculated position of optic will generally be given in this embodiment in terms of the "postoperative vitreous length" (VLpost), which is defined herein as the distance from the back of the IOL to the retina.

In certain embodiments, a highly predictive formulation of VLpost is calculated based on the following mathematical relationship which includes VLpre, ACDpre, and LT:

$$VL\,post = C1 + C2*VL\,pre + C3*ACD\,pre + C4*LT, \qquad (1)$$

where VLpre is the preoperative vitreous length of the eye measured as the difference between the AL and the ACDpre plus LT. ACDpre is the anterior chamber depth prior to an ocular surgical procedure as measured from the anterior corneal surface to the anterior lens surface, LT is the lens thickness, and C1-C4 are constants, that may depend on the IOL model. AL, ACDpre and LT may be measured with, for example the AC Master or other biometer and VLpre can be then be calculated from these measurements.

By way of non-limiting example, in certain 3 piece intraocular lens embodiments, constants for VLpost may be as follows: C1=−0.901; C2=0.982; C3=0.309; and C4=0.545.

In some embodiments, AL may be used rather than $VL_{pre}$ according to the following mathematical relationship: $VL_{post} = AL - (ACD_{pre} + 0.5\,LT)$. AL may be measured, for example, with the IOL Master. This illustrated embodiment was found to be highly predictive of $VL_{post}$ with $r^2=0.86$.

Another embodiment uses AL rather than $VL_{pre}$ according to the following mathematical relationship: $VL_{post}=C1+C2*AL+C3*ACD_{pre}+C4*LT$ where constants in certain 1 piece intraocular lens embodiments may be as follows: C1=−2.042; C2=0.944; C3=0.396; and C4=0.203. This illustrated embodiment was found to be highly predictive of $VL_{post}$ with $r^2=0.93$. By way of non-limiting example, in certain 3 piece intraocular lens embodiments, constants for $VL_{post}$ may be as follows: C1=−0.902; C2=0.983; C3=0.673; and C4=0.437. This illustrated embodiment was also found to be highly predictive of $VL_{post}$ with $r^2=0.98$.

In some embodiments, one or more of the measured variables may be left out. For example, the measurement of $ACD_{pre}$ may be left out and the coefficients for LT and $VL_{pre}$ may be evaluated according to the following mathematical relationship: $VL_{post}=−C1+C2*VL_{pre}+C3*LT$ where C1=1.63, C2=0.912, and C3=0.448. This illustrated embodiment was also found to be highly predictive of $VL_{post}$ with $r^2=0.86$.

Expanding further on this by leaving out LT, the coefficients for $VL_{pre}$ may be evaluated according to the following mathematical relationship: $VL_{post}=C1+C2*VL_{pre}$ where C1=4.734 and C2=0.842. This illustrated embodiment was also found to be highly predictive of $VL_{post}$ with $r^2=0.83$. The preoperative vitreous length was found to be a good predictor for the postoperative total power of the eye with $r^2=0.71$.

The systems and methods of the present invention may also incorporate a customized intraocular lens calculation such as is disclosed in U.S. Pat. No. 8,746,882, entitled "Customized Intraocular Lens Power Calculation System and Method," which is incorporated herein in its entirety. This embodiment generally includes measuring anterior and posterior corneal topography, an axial length (AXL), and an anterior chamber depth (ACD) of a subject eye, and for each of a plurality of intraocular lenses (IOLs), simulating the subject eye with the intraocular lens (IOL) implanted in accordance with the measuring, performing either monochromatic or polychromatic ray tracing through the surfaces defining the built eye model, calculating from the ray tracing a modulation transfer function (MTF)-based value, and selecting the IOL corresponding to a highest one of the MTF value for implanting in the subject eye. As used in this embodiment, the modulation transfer function (MTF) is one measurement of the quality of the system composed by the eye and the implanted IOL power. This function shows how an optical system transfers the frequency content from the object to the image. The higher the MTF value, the better the optical system. This function is closely related to contrast sensitivity measurements, and is also related to visual acuity when maximum contrast is considered. A human eye with excellent acuity can resolve about 30 sinusoidal cycles of black and white areas per degree, expressed in cycles per degree (cpd). Alternatively, MTF may be related to spatial frequency in terms of sinusoidal cycles of black and white areas distinguishable per millimeter, expressed as cycles per millimeter (cpmm), for example, 25, 50, or 100 cpmm. Spatial frequencies like 25 cpmm are especially interesting in vision, because the peak of contrast sensitivity related to the visual system is in this region. In this embodiment, the ray tracing may be performed polychromatically or monochromatically, depending on the IOL material, at a suitable entrance pupil, such as at or at about a 4 mm entrance pupil, for example. Further, the polychromatic ray tracing may be performed at about six (6) wavelengths weighted according the spectral sensitivity curve in photonic or mesopic conditions, although other suitable numbers of wavelengths may be used according to the present invention. calculating of the radially averaged polychromatic modulation transfer function (RpMTF) (or its monochromatic version (RMTF) if a monochromatic ray tracing is performed) value may be with regard to a single optical resolution, herein referred to as "point values," such as with respect to calculation of the RpMTF/RMTF at or at about 25 cpmm. Alternatively, Calculating from the ray tracing of the RpMTF/RMTF value may comprise calculating the area under a RpMTF/RMTF curve, wherein each curve pertains to the RpMTF/RMTF at a plurality of optical resolutions. Those skilled in the art will recognize that MTF Volume, Visual Strehl ratio or other suitable optical metrics for predicting the optical quality for each individual IOL model in the customized eye model may be used.

In this embodiment, the system and method may further include measuring a plurality of characteristics of a subject eye, and, with respect to at least one characteristic for each of a plurality of identified IOLs, predicting a position of the identified IOL when implanted in the subject eye, simulating the subject eye based on the plurality of characteristics, perform a ray tracing based on the customized eye model, calculating from the ray tracing a point from the RpMTF/RMTF value, and comparing a plurality of RpMTF/RMTF values corresponding to the plurality of considered IOLs to identify a highest one of RpMTF/RMTF values. Further, the method preferably including identifying one IOL from the plurality of IOLs corresponding to the highest one of RpMTF/RMTF values, and may include outputting the identified one of the IOLs.

Other systems and method that may be used in connection with the present invention include the following, all of which are incorporated herein by reference in their entirety: U.S. Pat. No. 8,696,119, entitled "Systems and Method for Determining Intraocular Lens Power"; U.S. Patent Publ. No. 20014/0253877, entitled, "Intraocular Lens that Matches an Image Surface to a Retinal Shape and Method of Designing Same"; U.S. Patent Publ. No. 2013/0335701, entitled "Lenses, Systems and Method for Providing Custom Aberration Treatments and Monovision to Correct Presbyobpia"; U.S. Pat. No. 8,623,081, entitled "Apparatus, System and Method of Intraocular Lens Power Calculation Using a Regression Formula Incorporate Corneal Spherical Aberration"; U.S. Patent Publ. No. 2013/08282116, entitled "Apparatus, System and Method to Account for Spherical Aberration at the Iris Plane in the Design of an Intraocular Lens"; U.S. Patent Publ. No. 2013/0226294, entitled "Apparatus, System and Methods for Optimizing Peripheral Vision"; WO 2013/028992, entitled "Ophthalmic Devices, Systems and Method for Optimizing Peripheral Vision"; U.S. Pat. No. 8,430,508, entitled "Single Microstructure Lens, Systems And Methods,"; U.S. Pat. No. 8,848,0228, entitled "Limited Echelette Lens, Systems And Methods"; and U.S. Pat. No. 8,444,267, entitled, "Ophthalmic Lens, Systems And Methods Having At Least One Rotationally Asymmetric Diffractive Structure.

All other patents and patent applications cited here are hereby incorporated by reference hereby reference in their entirety. Also, U.S. Patent Publication No. 2009/0161090, entitled "Systems and Methods for Measuring the Shape and Location of an Object," is hereby incorporated by reference in its entirety.

The use of the terms "a" and "an" and "the" and similar referents in the context of describing the invention (especially in the context of the following claims) are to be construed to cover both the singular and the plural, unless otherwise indicated here or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values here are merely intended to serve as a shorthand method of referring individually to each separate value falling within the range, unless otherwise indicated herein, and each separate value is incorporated into the specification as if it were individually recited herein. All methods described here can be performed in any suitable order unless otherwise indicated here or otherwise clearly contradicted by context. The use of any and all examples, or exemplary language (e.g., "such as") provided herein, is intended merely to better illuminate embodiments of the invention, and does not pose a limitation on the scope of the invention unless otherwise claimed. No language in the specification should be construed as indicating any non-claimed element as essential to the practice of the invention.

While certain illustrated embodiments of this disclosure have been shown and described in an exemplary form with a certain degree of particularity, those skilled in the art will understand that the embodiments are provided by way of example only, and that various variations can be made and remain within the concept without departing from the spirit or scope of the invention. Such variations would become clear to one of ordinary skill in the art after inspection of the specification, drawings and claims herein. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

We claim:

1. A system for selecting an intraocular lens (IOL) for implantation in a subject eye, comprising:
   a corneal topography subsystem;
   a wavefront aberrometer subsystem;
   an optical coherence tomography subsystem;
   a memory, which stores data of eye characteristics for the subject eye acquired from each of the corneal topography subsystem, the wavefront sensor subsystem and the optical coherence tomography subsystem, wherein the stored data includes a plurality of ocular biometry information, anterior corneal surface information, posterior corneal surface information, anterior lens surface information, and posterior lens surface information, lens tilt information, lens thickness and lens position information;
   wherein the memory further stores IOL model data for a plurality of IOL models, each IOL model having associated with it a plurality of predetermined parameters including dioptic power, anterior and posterior radius, IOL thickness, refractive index and dispersion, asphericity, toricity, echelette features, haptic angulation, and lens filter; and
   a processor coupled to the memory, the processor configured to derive a treatment of the subject eye, including, for each of the plurality of IOL models, to:
   (1) predict a position of the IOL model when implanted in the subject eye, based on the plurality of eye characteristics;
   (2) simulate the subject eye to produce an eye model based on the plurality of IOL predetermined parameters including the dioptic power, the anterior and posterior radius, the IOL thickness, the refractive index and dispersion, the asphericity, the toricity, the echelette features, the haptic angulation, and the lens filter, and the predicted IOL position;
   (3) perform ray tracing and an IOL spherical equivalent (SE) and cylinder (C) power calculation, as well as determine an optimum IOL orientation based on said eye model; and
   (4) propose one IOL power for one or more IOL models from the plurality of IOL models corresponding to the optimum IOL orientations based on predetermined criteria; and
   (5) show simulated optical quality and/or visual performance provided by each of the proposed IOL models for distance and/or for vergence and/or field angle.

2. The system of claim 1, wherein step (3) further includes to calculate from the ray tracing a modulation transfer function (MTF) value of the subject eye with the IOL model implanted, wherein the MTF is descriptive of transfer of frequency content from objects to images by the subject eye with the IOL model implanted, and
   wherein step (4) includes comparing a plurality of calculated MTF values corresponding to the plurality of IOL models to identify a highest one of the MTF values, and identifying one IOL model from the plurality of IOL models corresponding to the highest one of the MTF values.

3. The system of claim 2, wherein the MTF is a radially averaged polychromatic modulation transfer function (RpMTF) or a monochromatic modulation transfer function (RMTF).

4. A method of selecting an intraocular lens (IOL) to be implanted in a subject eye, comprising:
   measuring a plurality of eye characteristics for the subject eye comprising ocular biometry information, anterior corneal surface information, posterior corneal surface information, anterior lens surface information, and posterior lens surface information, lens tilt information, lens thickness information and lens position information; and
   storing in a memory a plurality of IOL models, each model having associated with it a plurality of predetermined parameters including dioptic power, refractive index and dispersion, anterior and posterior radius, IOL thickness, asphericity, toricity, echelette design, haptic angulation, and lens filter; and
   for each of the plurality of IOL models:
   (1) modeling the subject eye with the IOL model to predict a position of the IOL model when implanted in the subject eye;
   (2) simulating the subject eye to produce an eye model based on the plurality of IOL predetermined parameters including the dioptic power, the anterior and posterior radius, the IOL thickness, the refractive index and dispersion, the asphericity, the toricity, the echelette features, the haptic angulation, and the lens filter, and the predicted IOL position;
   (3) performing a ray tracing and an IOL spherical equivalent (SE) and cylinder (C) power calculation, as well as determining an optimum IOL orientation based on said eye model; and (4) proposing one IOL power for one or more IOL models from the plurality of IOL models corresponding to the optimum IOL orientations based on predetermined criteria; and (5) showing simulated optical quality and/or visual performance provided by each of the proposed IOL models for distance and/or for vergence and/or field angle.

5. The method of claim 4, wherein step (3) further includes calculating from the ray tracing a modulation transfer function (MTF) value of the subject eye with the IOL model implanted, wherein the MTF is descriptive of transfer of frequency content from objects to images by the subject eye with the IOL model implanted, and wherein step (4) includes comparing a plurality of calculated MTF values corresponding to the plurality of IOL models to identify a highest one of the MTF values, and identifying one IOL model from the plurality of IOL models corresponding to the highest one of the MTF values.

6. The method of claim 5, wherein the MTF is a radially averaged polychromatic modulation transfer function (RpMTF) or a monochromatic modulation transfer function (RMTF).

7. A tangible computer-readable storage device storing computer instructions which, when read by a computer, cause the computer to perform a method comprising:

receiving a plurality of eye characteristics for a subject eye comprising ocular biometry information, anterior corneal surface information, posterior corneal surface information, anterior lens surface information, and posterior lens surface information, lens tilt information, lens thickness information and lens position information;

storing in a memory a plurality of IOL models, each model having associated with it a plurality of predetermined parameters including dioptic power, refractive index and dispersion, anterior and posterior radius, IOL thickness, asphericity, toricity, echelette design, haptic angulation, and lens filter; and for each of the plurality of IOL models:

(1) simulating a geometry of the subject eye with each of the plurality of intraocular lenses (IOL) implanted, in accordance with the plurality of eye characteristics and the plurality of IOL predetermined parameters including the dioptic power, the anterior and posterior radius, the IOL thickness, the refractive index and dispersion, the asphericity, the toricity, the echelette features, the haptic angulation, and the lens filter, to produce an eye model;

(2) performing a ray tracing and an IOL spherical equivalent (SE) and cylinder (C) power calculation, as well as determining an optimum IOL orientation based on said eye model; and (3) proposing one IOL power for one or more IOL models from the plurality of IOL models corresponding to the optimum IOL orientations based on predetermined criteria; and (4) showing simulated optical quality and/or visual performance provided by each of the proposed IOL models for distance and/or for vergence and/or field angle.

8. The tangible computer-readable storage device of claim 7, wherein step (2) further includes calculating from the ray tracing a modulation transfer function (MTF) value of the subject eye with the IOL model implanted, wherein the MTF is descriptive of transfer of frequency content from objects to images by the subject eye with the IOL model implanted, and wherein step (3) includes comparing a plurality of calculated MTF values corresponding to the plurality of IOL models to identify a highest one of the MTF values, and identifying one IOL model from the plurality of IOL models corresponding to the highest one of the MTF values.

9. The tangible computer-readable storage device of claim 8, wherein the MTF is a radially averaged polychromatic modulation transfer function (RpMTF) or a monochromatic modulation transfer function (RMTF).

\* \* \* \* \*